US011192922B2

(12) United States Patent
McMurry et al.

(10) Patent No.: US 11,192,922 B2
(45) Date of Patent: Dec. 7, 2021

(54) SIGNAL MOLECULES AS CELL PENETRATION AGENTS

(71) Applicant: Kennesaw State University Research and Service Foundation, Inc., Kennesaw, GA (US)

(72) Inventors: Jonathan L. McMurry, Marietta, GA (US); John C. Salerno, Acworth, GA (US); Scott J. Nowak, Acworth, GA (US); Marcus C. Davis, Woodstock, GA (US); Kathleen Bartlow, Richmond, IN (US)

(73) Assignee: Kennesaw State University Research and Service Foundation, Inc., Kennesaw, GA (US)

( * ) Notice: Subject to any disclaimer, the term of this patent is extended or adjusted under 35 U.S.C. 154(b) by 0 days.

(21) Appl. No.: 16/848,214

(22) Filed: Apr. 14, 2020

(65) Prior Publication Data
US 2020/0385426 A1    Dec. 10, 2020

Related U.S. Application Data

(62) Division of application No. 16/074,923, filed as application No. PCT/US2017/016189 on Feb. 2, 2017, now Pat. No. 10,654,894.

(60) Provisional application No. 62/290,629, filed on Feb. 3, 2016.

(51) Int. Cl.
*C07K 7/08* (2006.01)
*A61K 47/64* (2017.01)
*C12N 9/12* (2006.01)
*C12N 9/16* (2006.01)

(52) U.S. Cl.
CPC ............... *C07K 7/08* (2013.01); *A61K 47/64* (2017.08); *C12N 9/12* (2013.01); *C12N 9/16* (2013.01); *C07K 2317/77* (2013.01); *C12Y 207/01* (2013.01); *C12Y 301/03* (2013.01)

(58) Field of Classification Search
CPC ......... G01N 33/6893; G01N 2800/065; G01N 2800/52; A61P 1/00; A61K 31/4035; A61K 31/4245; A61K 31/427; A61K 31/496; A61K 31/519; A61K 2039/505; A61K 2039/55; C07K 16/241; C07K 16/2839; C07K 2317/21; C07K 2317/24
See application file for complete search history.

(56) References Cited

U.S. PATENT DOCUMENTS

| | | | |
|---|---|---|---|
| 6,316,003 B1 | 11/2001 | Frankel et al. | |
| 6,589,503 B1 | 7/2003 | Piwnica-Worms | |
| 7,034,109 B2 | 4/2006 | Bonny | |
| 7,538,091 B2 | 5/2009 | Bonny | |
| 7,569,674 B2 | 8/2009 | Kohler et al. | |
| 7,662,178 B2 | 2/2010 | Marx et al. | |
| 7,727,958 B2 | 6/2010 | Li | |
| 7,754,678 B2 | 7/2010 | Guo et al. | |
| 7,927,580 B2 | 4/2011 | Cohen | |
| 8,067,532 B2 | 11/2011 | Maclean | |
| 8,080,517 B2 | 12/2011 | Bonny | |
| 8,183,339 B1 | 5/2012 | Bonny | |
| 8,236,924 B2 | 8/2012 | Bonny | |
| 8,273,867 B2 | 9/2012 | Dowdy et al. | |
| 8,278,413 B2 | 10/2012 | Bonny | |
| 8,524,673 B2 | 9/2013 | Li | |
| 8,569,447 B2 | 10/2013 | Bonny | |
| 8,748,395 B2 | 6/2014 | Bonny | |
| 2002/0013003 A1 | 1/2002 | Wagner et al. | |
| 2003/0161809 A1 | 8/2003 | Houston et al. | |
| 2006/0141549 A1 | 6/2006 | Mahajan et al. | |
| 2006/0281677 A1 | 12/2006 | Albarran et al. | |
| 2011/0027300 A1 | 2/2011 | Kamil et al. | |
| 2011/0190730 A1 | 8/2011 | Kirkland et al. | |
| 2016/0030510 A1 | 2/2016 | Lu et al. | |
| 2016/0122415 A1 | 5/2016 | Soucek et al. | |
| 2016/0304562 A1 | 10/2016 | Salerno | |
| 2016/0355561 A1 | 12/2016 | Salerno | |
| 2019/0031718 A1 | 1/2019 | McMurry et al. | |

FOREIGN PATENT DOCUMENTS

| | | |
|---|---|---|
| EP | 1544305 A1 | 6/2005 |
| EP | 1605893 A2 | 12/2005 |
| EP | 1964853 A1 | 9/2008 |
| EP | 3411387 A1 | 12/2018 |
| WO | 03/77931 A1 | 9/2003 |
| WO | 2004/030610 A2 | 4/2004 |
| WO | 2004/064780 A2 | 8/2004 |
| WO | 2004/078146 A2 | 9/2004 |
| WO | 2005/059129 A2 | 6/2005 |
| WO | 2009/067757 A1 | 6/2009 |
| WO | 2010/010112 A2 | 1/2010 |

(Continued)

OTHER PUBLICATIONS

Sultana et al.; "Measuring Protein-Protein and Protein-Nucleic Acid Interactions by Biolayer Interferometry"; Current Protocols in Protein Science; vol. 79; Feb. 2015; 26 pages.

(Continued)

*Primary Examiner* — Robert S Landsman
(74) *Attorney, Agent, or Firm* — Smith, Gambrell & Russell LLP

(57) ABSTRACT

Novel cell penetrating agents for intracellular delivery of desired cargo, including proteins. Use of cell penetrating agents to deliver cargos to the interior of cells and cellular compartments and organelles is transformative for diagnostic, therapeutic, and research processes.

18 Claims, 21 Drawing Sheets

Specification includes a Sequence Listing.

(56) References Cited

FOREIGN PATENT DOCUMENTS

| WO | 2015/134920 A1 | 9/2015 |
|---|---|---|
| WO | 2017/136534 A1 | 8/2017 |

OTHER PUBLICATIONS

Takahashi et al.; "Induction of pluripotent stem cells from fibroblast cultures"; Nature Protocols; vol. 2 No. 12; 2007; p. 3081-3089.

Takahashi et al.; "Induction of Pluripotent Stem Cells from Mouse Embryonic and Adult Fibroblast Cultures by Defined Factors"; Cell; vol. 126; Aug. 2006; p. 663-676.

Trabulo et al.; "Cell-penetrating Peptides as Nucleic Acid Delivery Systems: From Biophysics to Biological Applications"; Current Pharmaceutical Design; vol. 19 No. 16; 2013; p. 2895-2923.

Trabulo et al.; "Cell-penetrating peptides-mechanisms of cellular uptake and generation of delivery systems"; Pharmaceuticals; vol. 3; 2010; p. 961-993.

Usui et al.; "New Development of calmodulin and hyperextension mechanism new to control the pathogenesis of hyperextension function in the vascular system of the calmodulin-related proteins"; Folia Pharmacol. Japan; vol. 141; 2013; p. 85-89 (w/ English Translation).

Wadia et al.; "Transducible TAT-HA fusogenic peptide enhances escape of TAT-fusion proteins after lipid raft micropinocytosis"; Nature Medine; vol. 10; Mar. 2004; p. 310-315.

Wagstaff et al.; "Protein Transduction: Cell Penetrating Peptides and Their Therapeutic Applications"; Current Medicinal Chemistry; vol. 13 No. 12; May 2006; p. 1371-1387.

Weigel et al.; "Quantifying the dynamic interactions between a clathrin-coated pit and cargo molecules"; PNAS; Nov. 2013; p. E4591-E4600.

zur Hausen; "Immortalization of human cells and their malignant conversion by high risk human papillomavirus genotypes"; Cancer Biology; vol. 9; 1999; p. 405-411.

Abdiche et al.; "Determining kinetics and affinities of protein interactions using a parallel real-time label-free biosensor, the Octet"; Analytical Biochemistry; vol. 377; 2008; p. 209-217.

Bredt et al.; "Isolation on nitric oxide synthetase, a calmodulin-requiring enzyme"; Proc. Natl. Acad. Sci.; vol. 87(2); Jan. 1990; p. 682-685.

Capes-Davis et al.; "Check your cultures! A list of cross-contaminated or misidentified cell lines"; Int'l Journal of Cancer; vol. 127; 2010; 8 pages.

Cardozo et al.; "Cell-permeable peptides induce dose- and length-dependent cytotoxic effects"; Biochimica et Biophysica Acta; vol. 1768; 2007; p. 2222-2234.

Chaloin et al.; "Design of Carrier Peptide-Oligonucleotide Conjugates with Rapid Membrane Translocation and Nuclear Localization Properties"; Biochemical and Biophysical Research Communications; vol. 243; 1998; p. 601-608.

Copolovici et al.; "Cell-Penetrating Peptides: Design, Synthesis, and Applications"; ACS Nano; vol. 8 No. 3; 2014; p. 1972-1994.

Defilippis et al.; "Endogenous Human Papillomavirus E6 and E7 Proteins Differentially Regulated Proliferation, Senescence, and Apoptosis in Hela Cervical Carcinoma Cells"; Journal of Virology; vol. 77 No. 2; Jan. 2003; p. 1551-1563.

Dominici et al.; "Red blood cell-mediated delivery of recombinant HIV-1 Tat protein in mice induces anti-Tat neutralizing antibodies and CTL"; Vaccine; vol. 21; 2003; p. 2073-2081.

Dooley et al., Imaging Dynamic Redox Changes in Mammalian Cells with Green Fluorescent Protein Indicators; Journal of Biological Chemistry (May 21, 2004) vol. 279, No. 21, p. 22284-22293.

Eguchi et al., Efficient siRNA delivery by novel PTD-DRBD fusion proteins; Cell Cycle. (Feb. 1, 2010) vol. 9, No. 3, pp. 424-425.

El-Andaloussi et al.; "Cell-Penetrating peptides: mechanism and applications"; Curr. Pharma. Design; vol. 11; 2005; p. 3597-3611.

Elliott et al.; "Intercellular Trafficking and Protein Delivery by a Herpesvirus Structural Protein"; Cell; vol. 88; Jan. 1997; p. 223-233.

Erazo-Oliveras et al.; "Improving the Endosomal Escape of Cell-Penetrating Peptides and TheirCargos: Strategies and Challenges:"; Pharmaceuticals; vol. 5; 2012; p. 1177-1209.

Fonseca et al.; "Recent advances in the use of cell-penetrating peptides for medical and biological applications"; Advanced Drug Delivery Reviews; vol. 61; 2009; p. 953-964.

Gautam et al.; "CPPsite: a curated database of cell penetrating peptides"; Database; vol. 2012; 2012; 7 pages.

Geller et al.; "Molecular cloning and expression of inducible nitric oxide synthase from human hepatocytes"; Proc. Natl. Acad. Sci. USA; vol. 90; Apr. 1993; p. 3491-3495.

Glogau et al.; "Results of a Randomized, Double-Blind, Placebo-Controlled Study to Evaluate the Efficacy and Safety of a Botulinum Toxin Type A Topical Gel for the Treatment of Moderate-to-Severe Lateral Canthal Lines"; Journal of Drugs in Dermatology; vol. 11; Jan. 2012; p. 38-45.

Green et al.; "Autonomous functional domains of chemically synthesized human immunodeficiency virus Tat trans-activator protein"; Cell; vol. 55; 1988; p. 1179-1188.

Hirose et al.; "Transient Focal Membrane Deformation Induced by Arginine-rich Peptides Leads to Their Direct Penetration into Cells"; Molecular Therapy; vol. 20 No. 5; May 2012; p. 984-993.

Houdusse et al.; "Target sequence recognition by the calmodulin superfamily: Implications from light chain binding to the regulatory domain of scallop myosin"; Proc. Natl. Acad. Sci. USA; vol. 92; Nov. 1995; p. 10644-10647.

http://www.uniprot.org/uniprot/Q13555; UniProtKB—Q13555 (KCC2G_HUMAN); accessed Nov. 11, 2017; 19 pages.

Hudmon et al.; "Neuronal CA2+/Calmodulin-Dependent Protein Kinase II: The Role of Structure and Autoregulation in Cellular Function"; Annu. Rev. Biochem.; vol. 71; 2002; p. 473-510.

Johnson et al.; "Therapeutic applications of cell-penetrating peptides"; Cell Penetrating Peptides: Methods and Protocols, Methods in Molecular Biology; vol. 683; 2011; p. 535-551.

Krebs et al.; "Calcium-binding proteins and the EF-hand principle"; Calcium: A Matter of Life or Death; Chapter 3; 2007; p. 51-93.

Krossa et al.; "Down regulation of Akirin-2 increases chemosensitivity in human glioblastomas more efficiently than Twist-1"; Oncotarget; vol. 6 No. 25; Apr. 2015; p. 21029-21045.

Lonn et al.; "Cationic PTD/CPP-mediated macromolecular delivery: charging into the cell"; Expert Opinion on Drug Delivery; vol. 12; 2015; p. 1627-1636.

Lundberg et al.; "Cell Surface Adherence and Endocytosis of Protein Transduction Domains"; Molecular Therapy; vol. 8 No. 1; Jul. 2003; p. 143-150.

Macville et al.; "Comprehensive and Definitive Molecular Cytogenetic Characterization of Hela Cells by Spectral Karyotyping"; Cancer Research; vol. 59; Jan. 1999; p. 141-150.

Magzoub et al.; "Interaction and structure induction of cell-penetrating peptides in the presence of phospholipid vesicles"; Biochimica et Biophysica Acta; vol. 1512; 2001; p. 77-89.

Mantovani et al.; "The Human Papillomavirus E6 protein and its contribution to malignant progression"; Oncogene; vol. 20; 2001; p. 7874-7887.

Martin et al.; "Design, Synthesis and Characterization of a New Anionic Cell-Penetrating Peptide: SAP (E)"; Chembiochem; vol. 12(6); 2011; p. 896-903.

Mathisen et al.; "Visinin-like Protein (VILIP) Is a Neuron-specific Calcium-dependent Double-stranded RNA-binding Protien"; Journal of Biological Chemistry; vol. 274(44); Oct. 1999; p. 31571-31576.

McMurry et al.; "Rate, affinity and calcium dependence of nitric oxide synthase isoform binding to the primary physiological regulator calmodulin"; The FEBS Journal; vol. 278; 2011; p. 4943-4954.

McMurry et al.; "Weak Interactions between Salmonella enterica FlhB and Other Flagellar Export Apparatus Proteins Govern Type III Secretion Dynamics"; PLOS ONE; Aug. 2015; 14 pages.

Mcmurry: "Delivery of cargo molecules to cell interiors by a cell-penetrating peptide-tagged adaptor : The FASEB Journal", Apr. 1, 2015, XP055608618.

Mitchell et al.; "Polyarginine enters cells more efficiently than other polycationic homopolymers"; J. Peptide Res.; vol. 56; 2000; p. 318-325.

(56) References Cited

OTHER PUBLICATIONS

Montrose et al.; "Xentry, a new class of cell-penetrating peptide uniquely equipped for delivery of drugs"; Scientific Reports; vol. 3; 2013; 7 pages.
Morris et al.; "A new peptide vector for efficient delivery of oligonucleotides into mammalian cells"; Nucleic Acids Research; vol. 25 No. 14; 1997; p. 2730-2736.
Nowak et al.; "Akirin: A context-dependent link between transcription and chromatin remodeling"; BioArchitecture; vol. 2:6; 2012; p. 209-213.
Palm-Apergi et al.; "Do Cell-Penetrating Peptides Actually "Penetrate" Cellular Membranes?"; Molecular Therapy; vol. 20 No. 4; Apr. 2012; p. 695-697.
Payne et al.; "Calcium/Calmodulin-dependent Protein Kinase II"; The Journal of Biological Chemistry; vol. 263 No. 15; May 1988; p. 7190-7195.
Reissmann, Cell penetration: scope and limitations by the application of cell-penetrating peptides; Journal of Peptide Science (Oct. 2014) vol. 20, pp. 760-784.
Rickhag et al.; "Membrane-permeable C-terminal Dopamine Transporter Peptides Attenuate Amphetamine-evoked Dopamine Release"; The Journal of Biological Chemistry; vol. 288 No. 38; Sep. 2013; p. 27534-27544.
Saalik et al.; "Protein Cargo Delivery Properties of Cell-Penetrating Peptides. A Comparative Study"; Bioconjugate Chem.; vol. 15; 2004; p. 1246-1253.
Salerno et al., Novel cell penetrating peptide-adaptors effect intracellular delivery and endosomal escape of protein cargos; Journal of Cell Science; vol. 129, pp. 893-897; advanced online publication Jan. 22, 2016, Retrieved from the internet: <URL: http://jcs.biologists.org/content/joces/early/2016/01/21/jcs.182113.full.- pdf.
Sebbage; "Cell-penetrating peptides and their therapeutic applications"; Bioscience Horizons; vol. 2 No. 1; Mar. 2009; p. 64-72.
Soughayer et al.; "Characterization of TAT-Mediated Transport of Detachable Kinase Substrates"; Biochemistry; vol. 43; 2004; p. 8528-8540.
Stratton et al.; "Structural studies on the regulation of CA2+/calmodulin dependent protein kinase II"; Current Opinion in Structural Biology; vol. 23; 2013; p. 292-301.
Conner, Sean D., et al.; "Regulated portals of entry into the cell"; Nature; vol. 422; Mar. 6, 2003; p. 37-44.
Manufacturing Chemist; "CPPs: beating drug delivery barriers"; Jan. 26, 2015; retrieved from https://www.manufacturingchemist.com/technical/article_page/CPPs_beating_drug_delivery_barriers/104817 on Jul. 6, 2021; p. 1-7.
Fawell, Stephen, et al.; "Tat-mediated delivery of heterologous proteins into cells"; Proc. Natl. Acad. Sci. USA; vol. 91; Jan. 1994; p. 664-668.

FIG. 5

```
                                                                  *;   :       :
  1    ------------------------------------------------MADQLTEEQIAEF    13   CALM_
  1    ---------------------------------------------MTDQQAEARSYLSEEMIAEF  20   TNNC2
  1    ------------------------------------------MASGFKKPSAAGTGQFRKVAFPPELTEDQKQEV  33   CETN1
  1    ------------------------------------------------MAGELTPEEEAQY    13   CALL5
  1    MAAEHLLPGPFPSLADFALRAGGKGTERGSGS----GKPTGSGRGPRMARPLGQDQINEY    56   CALL4

:  .*.    *     *  *  ;.*  ....*    ::  ):      :* *  *. **,.
  14   REAFSLFDKDGDGTITTKELGTVMRSLGQNPTEAELQDMINEVDADGNGTIDFPEFLTMM    73   CALM_
  21   KAAFDMFDADGGGDISVKELGTVMRMLGQFPTKEELDAIIEEVDEDGSGTIDFEEFLVMM    80   TNNC2
  34   REAFGLFDVDGSGTIDAKELKVAMRALGFEFKKREMKNISEVDREGTGTISFNDFLAVM    93   CETN1
  14   KEAFSAVDTDGNGFISAQELGAALKATGERLSRAQLKRLISEYDSDGDGKISFQEFLTAA    73   CALL5
  57   KECFSLYDKQQRGKIKATDLMVAMRCLGASFTPGEVQRHLQTRGIDGNGELDFSTFLTIM    116  CALL4

::: .: .*          :*            *:  , :*::: :: :.*
  74   AREMKDT----DSEEEIREAFRVFDKDGNGYISAAELRHVMTNLGEKLTDEEVDEMIREAD   130  CALM_
  81   VRQMKEGAFGXSEEELAECFRIFDRNAIGYIDFEELAEIFRASGEHVTDEEIESLMKDGD   140  TNNC2
  94   TQKMSEK----LTKEEILKAFRLFDDDETGKISFKNLKRVANELGENLTDEELQEMIDEAD   150  CETN1
  74   KKAR------AGLEDLGVAFRAFDQDGLGHITVDELRRAMAGLGQPLPQEELDAMIREAD   127  CALL5
  117  HRQINQE---DPKKEILLAMLMVGKEKKGTVRASDLRSHLTSLGEKLTHKEVDDLFREAD   173  CALL4

131  IDGDGQVNYEEFVQMMTAK-----        149   P62158   CALM_HUMAN
  141  KNNGRIDFDEFLKMMEGVQ-----        165   P02585   TNNC2_HUMAN
  151  KDGDGEVNEEEFLKIMKKTSLY-        172   Q12798   CETN1_HUMAN
  128  VDQDGRVNYEEFARMLAQE-----        146   Q9NZT1   CALL5_HUMAN
  174  IEPSEKVKYDEFIRKITLPGRDY         196   Q9BXE6   CALL4_HUMAN
```

FIG. 6

```
   HM YGRKKRRQRRR         NOT1         MAGQLTEEQIAEFKE
AFSLFDKDGDGTITTKELGTVMRSLGQNPTEAELQDMINEVD
ADGNGTIDFPEFLTMMARKMKDTDSEEEIREAFRVFDKDGNG
YISAAELRHVITNLGEKLTDEEVDEMIREADIDGDGQVNYEEF
          VQMMTAK Stop Codon BamHI site KpnI site
```

FIG. 8A
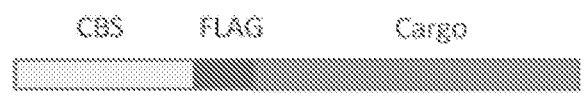
FIG. 8B
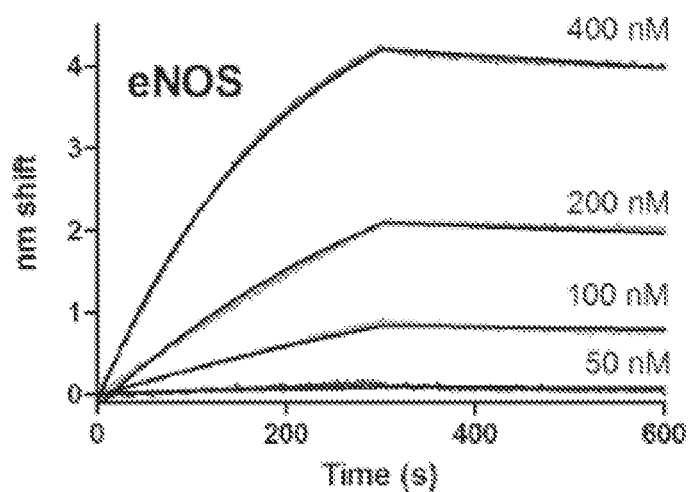

nucleus     cell

CBS-
tubulin nucleus     cell

CBS-E2

Control					E2:TAT-CaM 4 μM

Structure of expression control construct

SEQUENCE LISTING

<160> NUMBER OF SEQ ID NOS: 26

<210> SEQ ID NO 1
<211> LENGTH: 7
<212> TYPE: PRT
<213> ORGANISM: Artificial Sequence
<220> FEATURE:
<223> OTHER INFORMATION: Synthetic peptide

<400> SEQUENCE: 1

Pro Lys Lys Lys Arg Lys Val
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic peptide

<400> SEQUENCE: 2

Lys Arg Pro Ala Ala Thr Lys Lys Ala Gly Gln Ala Lys Lys Lys Lys
1               5                   10                  15

<210> SEQ ID NO 3
<211> LENGTH: 19
<212> TYPE: PRT
<213> ORGANISM: Artificial Sequence
<220> FEATURE:
<223> OTHER INFORMATION: Synthetic peptide

<400> SEQUENCE: 3

Lys Arg Arg Ala Ile Gly Phe Lys Lys Ala Glu Ala Val Phe Ser Ala
1               5                   10                  15

Lys Leu Met

<210> SEQ ID NO 4
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 4
tttttttttt tt                                                           12

<210> SEQ ID NO 5
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 5
aaaaaaaaaa aaaa                                                         14

<210> SEQ ID NO 6
<211> LENGTH: 13
<212> TYPE: PRT
<213> ORGANISM: Artificial Sequence
<220> FEATURE:
<223> OTHER INFORMATION: Synthetic peptide

<400> SEQUENCE: 6

Pro Gly Arg Lys Lys Arg Arg Gln Arg Arg Pro Pro Gln
1               5                   10

```
<210> SEQ ID NO 7
<211> LENGTH: 16
<212> TYPE: PRT
<213> ORGANISM: Artificial Sequence
<220> FEATURE:
<223> OTHER INFORMATION: Synthetic peptide

<400> SEQUENCE: 7

Arg Gln Ile Lys Ile Trp Phe Gln Asn Arg Arg Met Lys Trp Lys Lys
1               5                   10                  15

<210> SEQ ID NO 8
<211> LENGTH: 27
<212> TYPE: PRT
<213> ORGANISM: Artificial Sequence
<220> FEATURE:
<223> OTHER INFORMATION: Synthetic peptide

<400> SEQUENCE: 8

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 9
<211> LENGTH: 10
<212> TYPE: PRT
<213> ORGANISM: Artificial Sequence
<220> FEATURE:
<223> OTHER INFORMATION: Synthetic peptide

<400> SEQUENCE: 9

Phe Arg Glu Lys Leu Ala Tyr Ile Ala Pro
1               5                   10

<210> SEQ ID NO 10
<211> LENGTH: 24
<212> TYPE: PRT
<213> ORGANISM: Artificial Sequence
<220> FEATURE:
<223> OTHER INFORMATION: Synthetic peptide

<400> SEQUENCE: 10

Asp Ala Ala Thr Ala Thr Arg Gly Arg Ser Ala Ala Ser Arg Pro Thr
1               5                   10                  15

Glu Arg Pro Arg Ala Pro Ala Arg
            20

<210> SEQ ID NO 11
<211> LENGTH: 27
<212> TYPE: PRT
<213> ORGANISM: Artificial Sequence
<220> FEATURE:
<223> OTHER INFORMATION: Synthetic peptide

<400> SEQUENCE: 11

Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25

<210> SEQ ID NO 12
<211> LENGTH: 21
<212> TYPE: PRT
```

```
<213> ORGANISM: Artificial Sequence
<220> FEATURE:
<223> OTHER INFORMATION: Synthetic peptide

<400> SEQUENCE: 12

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide

<400> SEQUENCE: 13

Lys Ala Leu Ala Lys Ala Leu Ala Lys Ala Leu Ala
1               5                   10

<210> SEQ ID NO 14
<211> LENGTH: 18
<212> TYPE: PRT
<213> ORGANISM: Artificial Sequence
<220> FEATURE:
<223> OTHER INFORMATION: Synthetic peptide

<400> SEQUENCE: 14

Val Arg Leu Pro Pro Pro Val Arg Leu Pro Pro Pro Val Arg Leu Pro
1               5                   10                  15

Pro Pro

<210> SEQ ID NO 15
<211> LENGTH: 20
<212> TYPE: PRT
<213> ORGANISM: Artificial Sequence
<220> FEATURE:
<223> OTHER INFORMATION: Synthetic peptide

<400> SEQUENCE: 15

Gly Leu Phe Arg Ala Leu Leu Arg Leu Leu Arg Ser Leu Trp Arg Leu
1               5                   10                  15

Leu Leu Arg Ala
            20

<210> SEQ ID NO 16
<211> LENGTH: 8
<212> TYPE: PRT
<213> ORGANISM: Artificial Sequence
<220> FEATURE:
<223> OTHER INFORMATION: Synthetic peptide

<400> SEQUENCE: 16

Arg Arg Arg Arg Arg Arg Arg Arg
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide

<400> SEQUENCE: 17
```

Arg Arg Arg Arg Arg Arg Arg Arg
1               5

<210> SEQ ID NO 18
<211> LENGTH: 22
<212> TYPE: PRT
<213> ORGANISM: Artificial Sequence
<220> FEATURE:
<223> OTHER INFORMATION: Synthetic peptide

<400> SEQUENCE: 18

Leu Gly Thr Tyr Thr Gln Asp Phe Asn Lys Thr Phe Pro Gln Thr Ala
1               5                   10                  15

Ile Gly Val Gly Ala Pro
            20

<210> SEQ ID NO 19
<211> LENGTH: 18
<212> TYPE: PRT
<213> ORGANISM: Artificial Sequence
<220> FEATURE:
<223> OTHER INFORMATION: Synthetic peptide

<400> SEQUENCE: 19

Arg Gly Gly Arg Leu Ser Tyr Ser Arg Arg Arg Phe Ser Thr Ser Thr
1               5                   10                  15

Gly Arg

<210> SEQ ID NO 20
<211> LENGTH: 18
<212> TYPE: PRT
<213> ORGANISM: Artificial Sequence
<220> FEATURE:
<223> OTHER INFORMATION: Synthetic peptide

<400> SEQUENCE: 20

Leu Leu Ile Ile Leu Arg Arg Arg Ile Arg Lys Gln Ala His Ala His
1               5                   10                  15

Ser Lys

<210> SEQ ID NO 21
<211> LENGTH: 149
<212> TYPE: PRT
<213> ORGANISM: Homo sapiens

<400> SEQUENCE: 21

Met Ala Asp Gln Leu Thr Glu Glu Gln Ile Ala Glu Phe Lys Glu Ala
1               5                   10                  15

Phe Ser Leu Phe Asp Lys Asp Gly Asp Gly Thr Ile Thr Thr Lys Glu
                20                  25                  30

Leu Gly Thr Val Met Arg Ser Leu Gly Gln Asn Pro Thr Glu Ala Glu
            35                  40                  45

Leu Gln Asp Met Ile Asn Glu Val Asp Ala Asp Gly Asn Gly Thr Ile
        50                  55                  60

Asp Phe Pro Glu Phe Leu Thr Met Met Ala Arg Lys Met Lys Asp Thr
65                  70                  75                  80

Asp Ser Glu Glu Glu Ile Arg Glu Ala Phe Arg Val Phe Asp Lys Asp
                85                  90                  95

Gly Asn Gly Tyr Ile Ser Ala Ala Glu Leu Arg His Val Met Thr Asn
            100                 105                 110

Leu Gly Glu Lys Leu Thr Asp Glu Glu Val Asp Glu Met Ile Arg Glu

```
                    115                 120                 125
Ala Asp Ile Asp Gly Asp Gly Gln Val Asn Tyr Glu Glu Phe Val Gln
            130                 135                 140

Met Met Thr Ala Lys
145

<210> SEQ ID NO 22
<211> LENGTH: 160
<212> TYPE: PRT
<213> ORGANISM: Homo sapiens

<400> SEQUENCE: 22

Met Thr Asp Gln Gln Ala Glu Ala Arg Ser Tyr Leu Ser Glu Glu Met
1               5                   10                  15

Ile Ala Glu Phe Lys Ala Ala Phe Asp Met Phe Asp Ala Asp Gly Gly
            20                  25                  30

Gly Asp Ile Ser Val Lys Glu Leu Gly Thr Val Met Arg Met Leu Gly
        35                  40                  45

Gln Thr Pro Thr Lys Glu Glu Leu Asp Ala Ile Ile Glu Glu Val Asp
    50                  55                  60

Glu Asp Gly Ser Gly Thr Ile Asp Phe Glu Glu Phe Leu Val Met Met
65                  70                  75                  80

Val Arg Gln Met Lys Glu Asp Ala Lys Gly Lys Ser Glu Glu Glu Leu
                85                  90                  95

Ala Glu Cys Phe Arg Ile Phe Asp Arg Asn Ala Asp Gly Tyr Ile Asp
            100                 105                 110

Pro Glu Glu Leu Ala Glu Ile Phe Arg Ala Ser Gly Glu His Val Thr
        115                 120                 125

Asp Glu Glu Ile Glu Ser Leu Met Lys Asp Gly Asp Lys Asn Asn Asp
    130                 135                 140

Gly Arg Ile Asp Phe Asp Glu Phe Leu Lys Met Met Glu Gly Val Gln
145                 150                 155                 160

<210> SEQ ID NO 23
<211> LENGTH: 172
<212> TYPE: PRT
<213> ORGANISM: Homo sapiens

<400> SEQUENCE: 23

Met Ala Ser Gly Phe Lys Lys Pro Ser Ala Ala Ser Thr Gly Gln Lys
1               5                   10                  15

Arg Lys Val Ala Pro Lys Pro Glu Leu Thr Glu Asp Gln Lys Gln Glu
            20                  25                  30

Val Arg Glu Ala Phe Asp Leu Phe Asp Val Asp Gly Ser Gly Thr Ile
        35                  40                  45

Asp Ala Lys Glu Leu Lys Val Ala Met Arg Ala Leu Gly Phe Glu Pro
    50                  55                  60

Arg Lys Glu Glu Met Lys Lys Met Ile Ser Glu Val Asp Arg Glu Gly
65                  70                  75                  80

Thr Gly Lys Ile Ser Phe Asn Asp Phe Leu Ala Val Met Thr Gln Lys
                85                  90                  95

Met Ser Glu Lys Asp Thr Lys Glu Glu Ile Leu Lys Ala Phe Arg Leu
            100                 105                 110

Phe Asp Asp Asp Glu Thr Gly Lys Ile Ser Phe Lys Asn Leu Lys Arg
        115                 120                 125

Val Ala Asn Glu Leu Gly Glu Asn Leu Thr Asp Glu Glu Leu Gln Glu
```

```
            130                 135                 140
Met Ile Asp Glu Ala Asp Arg Asp Gly Asp Gly Val Asn Glu Glu
145                 150                 155                 160

Glu Phe Leu Arg Ile Met Lys Lys Thr Ser Leu Tyr
                165                 170
```

<210> SEQ ID NO 24
<211> LENGTH: 146
<212> TYPE: PRT
<213> ORGANISM: Homo sapiens

<400> SEQUENCE: 24

```
Met Ala Gly Glu Leu Thr Pro Glu Glu Ala Gln Tyr Lys Lys Ala
1               5                   10                  15

Phe Ser Ala Val Asp Thr Asp Gly Asn Gly Thr Ile Asn Ala Gln Glu
                20                  25                  30

Leu Gly Ala Ala Leu Lys Ala Thr Gly Lys Asn Leu Ser Glu Ala Gln
                35                  40                  45

Leu Arg Lys Leu Ile Ser Glu Val Asp Ser Asp Gly Asp Gly Glu Ile
50                  55                  60

Ser Phe Gln Glu Phe Leu Thr Ala Ala Lys Lys Ala Arg Ala Gly Leu
65                  70                  75                  80

Glu Asp Leu Gln Val Ala Phe Arg Ala Phe Asp Gln Asp Gly Asp Gly
                85                  90                  95

His Ile Thr Val Asp Glu Leu Arg Arg Ala Met Ala Gly Leu Gly Gln
                100                 105                 110

Pro Leu Pro Gln Glu Leu Asp Ala Met Ile Arg Glu Ala Asp Val
                115                 120                 125

Asp Gln Asp Gly Arg Val Asn Tyr Glu Glu Phe Ala Arg Met Leu Ala
            130                 135                 140

Gln Glu
145
```

<210> SEQ ID NO 25
<211> LENGTH: 196
<212> TYPE: PRT
<213> ORGANISM: Homo sapiens

<400> SEQUENCE: 25

```
Met Ala Ala Glu His Leu Leu Pro Gly Pro Pro Ser Leu Ala Asp
1               5                   10                  15

Phe Arg Leu Glu Ala Gly Gly Lys Gly Thr Glu Arg Gly Ser Gly Ser
                20                  25                  30

Ser Lys Pro Thr Gly Ser Ser Arg Gly Pro Arg Met Ala Lys Phe Leu
            35                  40                  45

Ser Gln Asp Gln Ile Asn Glu Tyr Lys Glu Cys Phe Ser Leu Tyr Asp
50                  55                  60

Lys Gln Gln Arg Gly Lys Ile Lys Ala Thr Asp Leu Met Val Ala Met
65                  70                  75                  80

Arg Cys Leu Gly Ala Ser Pro Thr Pro Gly Glu Val Gln Arg His Leu
                85                  90                  95

Gln Thr His Gly Ile Asp Gly Asn Gly Glu Leu Asp Phe Ser Thr Phe
                100                 105                 110

Leu Thr Ile Met His Met Gln Ile Lys Gln Glu Asp Pro Lys Lys Glu
                115                 120                 125

Ile Leu Leu Ala Met Leu Met Val Asp Lys Glu Lys Lys Gly Tyr Val
```

```
                130                 135                 140
Met Ala Ser Asp Leu Arg Ser Lys Leu Thr Ser Leu Gly Glu Lys Leu
145                 150                 155                 160

Thr His Lys Glu Val Asp Asp Leu Phe Arg Glu Ala Asp Ile Glu Pro
                165                 170                 175

Asn Gly Lys Val Lys Tyr Asp Glu Phe Ile His Lys Ile Thr Leu Pro
                180                 185                 190

Gly Arg Asp Tyr
        195

<210> SEQ ID NO 26
<211> LENGTH: 13
<212> TYPE: PRT
<213> ORGANISM: Artificial Sequence
<220> FEATURE:
<223> OTHER INFORMATION: Synthetic peptide

<400> SEQUENCE: 26

His Met Tyr Gly Arg Lys Lys Arg Arg Gln Arg Arg Arg
1               5                   10
```

SIGNAL MOLECULES AS CELL PENETRATION AGENTS

CROSS REFERENCE TO RELATED APPLICATIONS

This application is a divisional of and claims priority to and the benefit of U.S. Ser. No. 16/074,923 filed Aug. 2, 2018 (now U.S. Pat. No. 10,654,894), which is a 371 of PCT/US17/16189 filed Feb. 2, 2017, which claims benefit of 62/290,629 filed Feb. 3, 2016, each of which is hereby incorporated by reference in its entirety.

BACKGROUND

Agents such as peptides have been discovered or designed to be rapidly internalized by eukaryotic cells. Such cell-penetrating agents, which includes but are not limited to peptides, mediate penetration of the plasma membrane, permitting delivery of one or more macromolecules, also termed a cargo or cargos, to the cell interior. A cargo may be a protein, nucleic acid, liposome, drug, etc.

Typical cell penetrating peptides (CPP) are 10 to 30 amino acids in length. Typical CPP are classified as one of arginine-rich CPP, amphipathic and lysine-rich CPP, or hydrophobic CPP. When the macromolecule is a protein, CPP have been attached to the N-terminus, the C-terminus, and intermediate positions, using a variety of covalent or non-specific hydrophobic linkage methods, e.g., using cysteine thiols for targeting.

Representative known CPP include the following:

| Lysine rich CPPs and others derived from translocation domains | | | |
|---|---|---|---|
| Peptide types | Origin | Sequence | Cargo |
| Tat | HIV-Tat protein (46-58) | PGRKKRRQRRPPQ SEQ ID NO: 6 | Protein/peptide/siRNA/ liposome/nanoparticle |
| Penetratin | Homeodomain | RQIKIWFQNRRMKWKK SEQ ID NO: 7 | peptide/siRNA/ liposome |
| Transportan | Galanin-mastoparan | GWTLNSAGYLLGKINLKALAALAKKIL SEQ ID NO: 8 | Protein/peptide/siRNA |
| Dat | Dopamine transporter | FREKLAYIAP SEQ ID NO: 9 | Protein/peptide/siRNA |
| VP-22 | HSV-1 structural protein | DAATATRGRSAASRPTERPRAPAR-SASRPRRPVD SEQ ID NO: 10 | Protein |

| Amphipathic peptides | | | |
|---|---|---|---|
| Peptide types | Origin | Sequence | Cargo |
| MPG | HIV Gp41-SV40 | GALFLGFLGAAGSTMGAWSQPKKKRKV SEQ ID NO: 11 | siRNA/ODN/plasmid |
| Pep-1 | Trp-rich motif- SV40 NLS | KETWWETWWTEWSQPKKKRKV SEQ ID NO: 12 | Protein/peptide |
| MAP molecule/ | Chimeric | KALAKALAKALA SEQ ID NO: 13 | Small plasmid |
| SAP | Proline-rich motif | VRLPPPVRLPPPVRLPPP SEQ ID NO: 14 | protein/peptide |
| PPTG1 | Chimeric | GLFRALLRLLRSLWRLLLRA SEQ ID NO: 15 | Plasmid |

| Arginine rich and other cell-penetrating peptides | | |
|---|---|---|
| Peptide | Origin | Sequence / Cargo types |
| Oligoarginine | Chimeric | Agr8 or Arg9 SEQ ID NO: 16 and 17 / Protein/peptide/siRNA/ODN |
| hCT (9-32) | Human calcitonin | LGTYTQDFNKTFPQTAIGVGAP SEQ ID NO: 18 / Protein/plasmid DNA |

-continued

| | | |
|---|---|---|
| SynB | Protegrin Doxorubicin | RGGRLSYSRRRFSTSTGR SEQ ID NO: 19 |
| Pvec | Murine VE-Protein/peptide cadherin | LLIILRRRIRKQAHAHSK SEQ ID NO: 20 |

CPP are promising for use as diagnostics and therapeutics. While currently used in clinical trials and as research tools, limitations such as their penetration efficiency and endosomal entrapment have prevented their broad adoption as a method to alter the intracellular environment. Transcription-transactivating (TAT) peptides are short signal sequences that mediate transport of proteins across the membranes of many cells. TAT peptides were believed to directly mediate transport across phospholipid bilayers; they can drive uptake of large proteins that could not cross the membrane without an active uptake process. TAT peptides attach to membrane receptors and cause internalization in coated pits. Constructs are known that can be internalized by processes that rely on recognition of short TAT peptides attached as C or N terminal fusions. The growing consensus is that most, if not all, CPP are rapidly internalized by receptor-mediated endocytosis. However, they are not efficiently released into the cytoplasm, likely due to high affinity interactions between CPP and their receptors. Thus, covalently or hydrophobically linked CPP-cargos remain trapped in the endosomes. These cargo proteins also required purification as CPP adducts. This resulted in eukaryote expression complicated by binding to import machinery via the CPP, and complicated handling of the CPP because many desirable products were rendered potentially hazardous by the CPP tag.

The inventive system and method overcomes these and other detriments. The inventive system and method extends utility of TAT peptide and related CPP constructs by expressing CPP fusions of small proteins that strongly bind other proteins.

SUMMARY

In one aspect, a composition for intracellular delivery of a biomolecule is provided, where the composition comprises a cell penetrating peptide (CPP) or cell penetrating agent (CPA) covalently linked to an adapter, and a cargo molecule covalently linked to an adapter binding molecule, and the composition formed by non-covalent linkage between the adapter and adapter binding molecule. The composition comprises a cell penetrating peptide (CPP) or cell penetrating agent (CPA) covalently linked to an adapter, the adapter non-covalently linked to an adapter binding molecule, and a cargo molecule covalently linked to the adapter binding molecule, where the composition provides for intracellular delivery of the cargo. The composition for intracellular delivery of a biomolecule is provided, the composition comprises a cell penetrating peptide (CPP) or cell penetrating agent (CPA) covalently linked to an adapter, the adapter non-covalently linked to an adapter binding molecule, and the adapter binding molecule covalently linked to a cargo.

In one embodiment, the adapter is calmodulin or a calcium binding protein and the adapter binding molecule is a calmodulin binding peptide. In one embodiment, the CPP is selected from the group consisting of Tat, penetratin, transportan, Dat, VP-22, amphipathic peptides, MPG, Pep-1, MAP, SAP, PPTG1, arginine rich peptides, oligoarginine, hCT (9-32), SynB, and Pvec. In one embodiment, the CPA is selected from a receptor or transporter ligand, and the receptor is selected from the group consisting of insulin receptor, beta 2-adrenergic receptor, folate receptor, the N-methyl-D-aspartic acid (NMDA) receptor, opiate receptors, cannabinoid receptor, and combinations thereof, and the transporter is selected from the group consisting of dopamine transporter, serotonin transporter, norepinephrine transporter, endothelial glucose transporter, and combinations thereof.

In one embodiment, the adapter binding molecule is further attached to a sequence that localizes the cargo to a cellular location or organelle that is selected from the group consisting of nucleus, peroxisome, mitochondria, endoplasmic reticulum, Gogli, and combinations thereof. In one embodiment, the sequence is a nuclear localization sequence.

In various embodiments, the cargo is selected from the group consisting of a protein, a drug, a liposome, a nucleic acid, and combinations thereof.

In various embodiments, the non-covalent linkage between the adapter and the adapter binding molecule is reversible. In one embodiment, at least one characteristic of an intracellular environment promotes reversal of the non-covalent linkage between the adapter and the adapter binding molecule, resulting in release of the cargo from the CPP. In one embodiment, the characteristic is an intracellular calcium concentration.

In one embodiment, the cargo is selected from the group consisting of a modulator of transcription in the cell, a probe that measures a property of the cell interior, and an enzyme. In one embodiment, the enzyme is a kinase or a phosphatase. In one embodiment, the enzyme is modified to be constitutively active. In one embodiment, the probe is an oxidation monitor, a nitric oxide (NO) sensor, or a pH sensor. In one embodiment, the cargo is a nucleic acid and the adapter binding molecule is covalently linked to a nucleic acid binding protein.

In another aspect, a method for delivering a cargo inside a cell is provided. In one embodiment, the method comprises forming a complex by contacting a cell penetrating peptide (CPP) or cell penetrating agent (CPA) covalently linked to an adapter, with a cargo molecule covalently linked to an adapter binding molecule, under conditions suitable for forming a non-covalent bond between the adapter and adapter binding molecule, and contacting the cell with the complex under conditions sufficient to result in delivery of the cargo inside the cell. In one embodiment, the cell penetrating peptide (CPP) or cell penetrating agent (CPA) covalently linked to an adapter and the cargo molecule covalently linked to an adapter binding molecule are added separately to culture media containing the cell, and the complex forms in the culture media.

In one embodiment, the adapter is calmodulin or a calcium binding protein and the adapter binding molecule is a calmodulin binding peptide. In one embodiment, the CPP is selected from the group consisting of Tat, Penetratin, Transportan, Dat, VP-22, Amphipathic peptides, MPG, Pep-1, MAP, SAP, PPTG1, arginine rich peptides, Oligoarginine, hCT (9-32), SynB, and Pvec. In one embodiment, the CPA is selected from the group consisting of a receptor or transporter ligand. In one embodiment, the receptor is selected from the group consisting of insulin receptor, beta 2-adrenergic receptor, folate receptor, the N-methyl-D-aspartic acid (NMDA) receptor, opiate receptors, and cannabinoid receptor, and the transporter is selected from the group consisting of dopamine transporter, serotonin transporter, norepinephrine transporter, and endothelial glucose transporter.

In one embodiment, the adapter binding molecule is also bound to a localization sequence. In one embodiment, the localization sequence is a nuclear localization sequence.

In one embodiment, the cargo is at least one of a protein, a drug, a liposome, or a nucleic acid.

In one embodiment, the non-covalent linkage between the adapter and the adapter binding molecule is reversible. In various embodiments, at least one characteristic of an intracellular environment promotes reversal of the non-covalent linkage between the adapter and the adapter binding molecule, resulting in release of the cargo from the CPP. In one embodiment, the characteristic is an intracellular calcium concentration.

In one embodiment, the cargo is selected from the group consisting of a modulator of transcription in the cell, a probe that measures a property of the cell interior, an enzyme, and combinations thereof. In one embodiment, the enzyme is a kinase or a phosphatase. In one embodiment, the enzyme is modified to be constitutively active. In one embodiment, the probe is selected from the group consisting of an oxidation monitor, a NO sensor, a pH sensor, and combinations thereof.

In one embodiment, the cargo is a nucleic acid and the adapter binding molecule is covalently linked to a nucleic acid binding protein.

BRIEF DESCRIPTION OF THE DRAWINGS

FIG. 3A shows that excitation of D leads to emission from A only when A and D are in proximity due to complex formation, also reducing donor emission. FIG. 3B shows that when A and D are not in proximity, there is no emission from A. Examples of donor acceptor pairs with good overlap include Alexa Fluor 488 and Alexa Fluor 647.

FIG. 5 shows sequence alignment of human calmodulin 1 (CALM) and four "calmdulin-like proteins". The similarity of these human calmodulin homologs is much less than the similarity of human and C. elegans calmodulin; less than 2% of the positions are identically conserved. The sequences shown are, from top to bottom, SEQ ID NOS: 21-25.

FIG. 6 shows the amino acid sequence of TAT-CaM, a CPP tagged calmodulin. The short CPP binding sequence (SEQ ID NO: 26), which contains amino acids 47-57 of SEQ ID NO: 6 (TAT), is located directly before the NOT1 site, which is followed by CaM (SEQ ID NO: 21).

FIG. 7A shows nNOS added without CPP adapter. Background still shows stained nNOS after washing with media. Some nNOS adheres to the cell surface; three-dimensional cross sections show no nNOS inside cells. FIG. 7B shows that in the presence of TAT-CaM, a large amount of nNOS is rapidly and actively pumped inside the cell, clearing the intracellular space and protecting nNOS from removal by washing. The cell boundary is now visible because cytoplasm is stained by released nNOS. Three dimensional cross sections confirm that labeled nNOS is inside the cells. Circles (yellow) inside cells are labeled endosomes.

FIGS. 8A-8F show a design of TAT-CaM and cargo proteins, according to one embodiment, and dissociation data for various embodiments. FIG. 8A shows a schematic of TAT-CaM and cargo proteins with amino termini at left. FIGS. 8B-8E show biolayer interferometry (BLI) analysis of TAT-CaM binding to (FIG. 8B) purified endothelial nitric oxide synthase; (FIG. 8C) CBS-β-Gal; (FIG. 8D) CBS-HRP; and (FIG. 8E) CBS-myoglobin. TAT-CaM was biotinylated and bound to streptavidin (SA) sensors. Reference-subtracted raw data are rendered as points with fits to a global single-state association-then-dissociation model. Analyte concentrations are noted for each trace. Association and dissociation phases were 300s in length. FIG. 8F shows dissociation data of the constructs of FIGS. 8C-8E after dissociation in buffer only.

FIG. 11F shows the calcium-dependent binding for all constructs in FIGS. 11A-11E.

Figure 1:
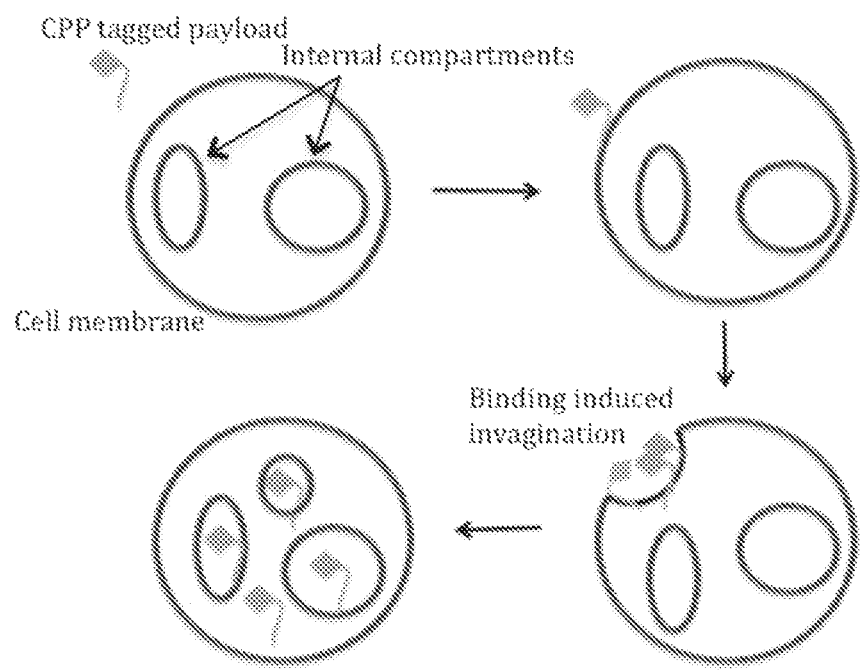
FIG. 1 shows a scheme for cellular uptake of cargo tagged with a cell penetrating peptide (CPP), where uptake of CPP bound cargo proceeds clockwise from upper left by binding to membrane and invagination; depending on the CPP tag, cargo may be targeted to internal compartments such as nuclei, mitochondria, etc., or to the cytoplasm.

The disclosed CPP-adapter constructs, schematically represented as

CPP------adapter--adapter binding molecule------cargo where the longer darker line indicates a covalent bond, and where the shorter lighter line indicates a non-covalent bond, overcomes these and other problems.

As only one non-limiting example, the construct of CPP=HIV transactivator of transcription (TAT), the adapter=calmodulin (CaM), and cargo contains a calmodulin binding site, the construct overcomes the limitations of covalently fused CPP-cargo constructs. Automatic internal release from the CPP is effected upon construct entry into a cell, because most mammalian cells maintain low resting calcium concentrations, facilitating escape of the construct from endosomal degradation.

The mechanism(s) by which CPP cellular uptake occurs is under investigation; however, several pathways appear to be used. In part, this reflects differences among the CPP themselves, but the same CPP may be taken up by different pathways under different circumstances.

The initial interaction between cellular membranes and CPP-protein constructs is through interactions with membrane surface hydrophobic components and/or negatively charged groups, such as phospholipids and heparin sulfate proteoglycans. The constructs that are membrane-associated, but not yet translocated, are difficult to distinguish from translocated groups, except by advanced three dimensional methods (e.g., confocal microscopy). This difficulty has led to artifacts in the study of CPP mechanisms. Once the CPP construct is associated with the membrane surface, several translocation mechanisms may be used. For example, there is evidence for clathrin dependent endocytosis, caveolin dependent endocytosis, and macropinocytosis for different construct combinations, i.e., CPP and cargo.

Since discovery of the Tat peptide (TaTp), a variety of CPP have been found to enable transport of macromolecular cargos to both cells in culture and in animals. Well characterized CPP originating from the N- or C-termini of viral proteins include TATp, oligoarginines, MPG peptides, Pep1, and VP22.

The TAT CPP derived from the carboxy terminus of the dopamine transporter can translocate large cargos. For example, the 1,024 amino acid *E. coli* β-galactosidase can be transported. It exists as a 464-kDa homotetramer with each subunit having five domains: jelly-roll type barrel, two fibronectin type III-type barrels, a β-sandwich domain, and a TIM-type barrel domain that contains the catalytic site. The CPP tag can enable translocation of such a multimer of modular components.

Versatile translocation systems that use CPP tags to produce novel systems to transport cargo and manipulate the interior of cells are disclosed.

Adapter molecules that make strong protein-protein interactions and are linked to CPP are disclosed.

The inventive constructs provide a convenient and powerful method to perturb cell interiors. The constructs may contain many potential cargos and may be selective CPP. The invention is thus not limiting to a particular component of the construct.

Non-limiting examples of the adapter, which is covalently bound to CPP, are disclosed. In one embodiment, the adapter is calmodulin or a related calcium binding protein. In one preferred embodiment, the CPP is TAT or another CPP listed in Table 2. In one embodiment, the adapter releases its cargo after targeting to an interior cellular compartment. In one embodiment, such targeting takes advantage of the low calcium environments in many compartments. In one embodiment, the adapter uses protein-ligand interactions to bind the cargo by an adapter binding molecule, where the adapter binding molecule is non-covalently linked to the adapter and is covalently linked to the cargo. In one embodiment, the construct of a CPP covalently bound to an adapter, which may be referred to as a CPP tagged adapter, incorporates G protein subunits with slow GTPase activity to release cargos internally after GTP hydrolysis. In one embodiment, the CPP tagged adapter molecule uses internal enzymatic activity, e.g., kinase or phosphatase activity, to release cargoes in the cell interior.

One embodiment is a method using CPP tagged adapters as previously described to deliver a cargo to the interior of cells either in culture or in vivo. Applications include, but are not limited to, internal measurements of conditions including pH, calcium, oxygen, and nitric oxide concentration, and delivery of reagents to internal compartments to map the location of cell components using protein-protein interactions. In one embodiment, the cargo delivered to internal compartments detects and measures the presence of proteins and nucleic acids in vivo or in situ in cultured or isolated cells. In one embodiment, the cargo is a fluorescence tagged Fab antibody fragment, and the target may be an internal pathogen so the method is used for diagnosis of a pathology. In one embodiment, the cargo delivered to internal compartments perturbs the cellular state, e.g., metabolic state, developmental state, etc., in vivo or in situ. In one embodiment, the cargo is a constitutively active protein that is a phosphorylation mutant of kinases at activating sites. In one embodiment, the cargo delivered inside a cell and/or to internal compartments modifies expression, e.g., repressors or enhancers of gene expression, and small RNAs such as siRNA and miRNA. In one embodiment, the cargo is delivered to treat diseases resulting in part from internal pathogens. In one embodiment, the cargo is an antibody or antibody fragment. In one embodiment, the cargo is a specific enzyme, a ligand, or a small RNA. In one embodiment, the cargo is delivered to treat a metabolic disorder or symptoms of a metabolic disorder, such as delivering fah to treat hereditary tyrosinemia. In one embodiment, the cargo is a constitutively active modified kinase. In one embodiment, the cargo is delivered to modify the genome of an organism.

Methods that integrate protein purification and cell entry use the attachment mechanism as an affinity ligand for chromatography.

In one embodiment where the cargo is a protein, the cargo has a calmodulin binding peptide as an N- or C-terminal extension, and is then purified on a calmodulin affinity column and delivered internally by CPP tagged calmodulin. In one embodiment where the cargo is a nucleic acid or small molecule, the calmodulin binding peptide is covalently linked to the nucleic acid or small molecule.

In one embodiment, the cargo is a Cas protein linked to a calmodulin binding peptide, and may also be linked to a nuclear localization sequence, and CPP allows delivery of Cas to the cell interior. Cas may be used for genome modification, including gene knock-out and gene knock-in modifications.

As one example, the method delivers a CRISPR/Cas complex to the cell interior, using a Cas construct with a CaM binding peptide/adapter binding molecule with TAT-CaM or other CPP-adapter. This example may be used for extensive downstream applications including, but not limited to, protocols for using CRISPR/CRISPRi in living organisms, such as animals and plants, cell lines with low efficiency of success using conventional CRISPR-based techniques, antiviral applications, antiparasitic applications, chemotherapeutic agents using CRISPR gene editing to introduce mutations or CRISPRi to manipulate expression of essential genes.

Other uses include delivery of therapeutics for autoimmune diseases with genetic components (e.g. celiac disease, rheumatoid arthritis, etc.), potentially-fatal or disabling childhood genetic diseases (e.g. Tay-Sachs, PKU, Duchenne's muscular dystrophy, beta-thalassemia, sickle-cell anemia, etc.), and neurological disorders including Huntington's disease, Alzheimer's disease, some forms of Parkinson's disease, amyotrophic lateral sclerosis, etc. CRISPR and CRIPSR1 is also used for topical therapies, e.g., for severe eczema and other skin conditions.

The method and construct may be used in industrial applications. Examples include rapid modification of single-celled organisms, e.g. bacteria and algae, biofuel production, rapid modification of organisms used in industrial chemical production, rapid modification of genetic organisms used to produce biologics, e.g., insulin, growth hormone, etc. The compositions and methods also are used in agricultural applications, e.g., rapid genetic modification of livestock, optimization of animal husbandry applications involving recombinant DNA, modification of domesticated crops for feedstocks and human food consumption, modification of crops used in biofuel applications, etc.

The CPP tagged adapters reversibly bind an adapter binding molecule tagged cargo by non-covalent bonds then release the cargo in the cell interior, which may include targeting to one or more internal cellular compartment, e.g., nucleus, mitochondria, peroxisomes, endoplasmic reticulum, etc. The stable but reversible adapter coupling the CPP to a cargo has applications and advantages in safety, utility, and in ease of cargo purification. The term 'adapter' has been used in reference to the CPP itself, not to a coupling intermediate.

Ideal adapters are small, stable, readily purified proteins capable of strong interaction with the cargo, either alone by intrinsic protein-protein interactions, or via an adapter binding molecule, e.g., a group such as biotin covalently bound to the cargo. This advantageously allows a cargo protein to be purified by affinity chromatography using an N- or C-terminal extension, and the same extension can be used to mediate cargo binding to the CPP tagged adapter.

This also provides other advantages. This scheme allows production of cargos with only a single tag, rather than a CPP adapter and an affinity tag. This scheme also requires only a few CPP tagged adapters to be developed to deliver many different cargos; significant because the direct CPP tagged versions of many potential cargos carry a potential risk to workers involved in their purification due to the cell membrane permeability enhancement. Production of a limited number of relatively benign CPP-adapter constructs, under well-controlled conditions, provides a significant safety factor, and the adapter-cargo complex need only be assembled at the point of use, and in cases where construct formation is faster than uptake by cells, even being added separately to cell cultures.

The CPP-adapter-cargo construct can be designed to dissociate on cellular internalization. One convenient way of doing this is to use an adapter that responds to the internal cellular conditions. Other methods, e.g., an unstable linkage, autocatalytic dissociation, photodissociation, etc., are also possible. The use of calcium by mammalian cells as a signal provides an avenue for cargo release; cell interiors are normally maintained at very low levels of calcium by ATP-driven pumps, and cells contain a variety of calcium biosensors that respond to transient calcium increases to tightly bind and release target peptides. In one embodiment, the adapter protein is a calcium biosensor such as calmodulin.

Calmodulin (CaM) is a small (16.7 kDa), soluble, heat resistant, multifunctional calcium biosensor protein that is the major mediator of calcium signaling in mammalian cells. When calcium is present, the CaM protein folds into a dumbbell-shaped configuration with two connected globular regions; each end of the globular "dumbbell" contains two calcium-binding EF hands. The alpha helix connector breaks, and closes around targets containing a 17 amino acid canonical motif or one of several alternative target motifs. CaM binds to targets with high affinity, in the picomolar range, and is typically diffusion limited. CaM is the archetypical member of the EF hand-calmodulin superfamily of calcium signaling proteins. It is easy to produce CaM site-directed mutants and constructs; production of novel CaM constructs provides unique and valuable reagents.

The invention extends the usefulness of TAT peptide constructs, and related CPP constructs, by expressing TAT fusions of small adapters that strongly bind other molecules. Specifically, TAT-calmodulin is readily taken up in whole organisms and by cells in culture, such as CHO cells. TAT was used as the initial CPP tag because of prior success in producing TAT tagged proteins that are taken up by mammalian cells. Other CPP tagged calmodulins, such as antennapedia-CaM, SAP-CaM and SAP(E)-CaM, an engineered anionic version of SAP (Martin et al., Chembiochem, 12(6), 896-903 (2011)), as well as TAT fusions with other CaM binding proteins, such as TAT-troponin and TAT-calmodulin-like protein 3 (CALM3) have been made and shown to work in nearly identical fashion.

Figure 2:
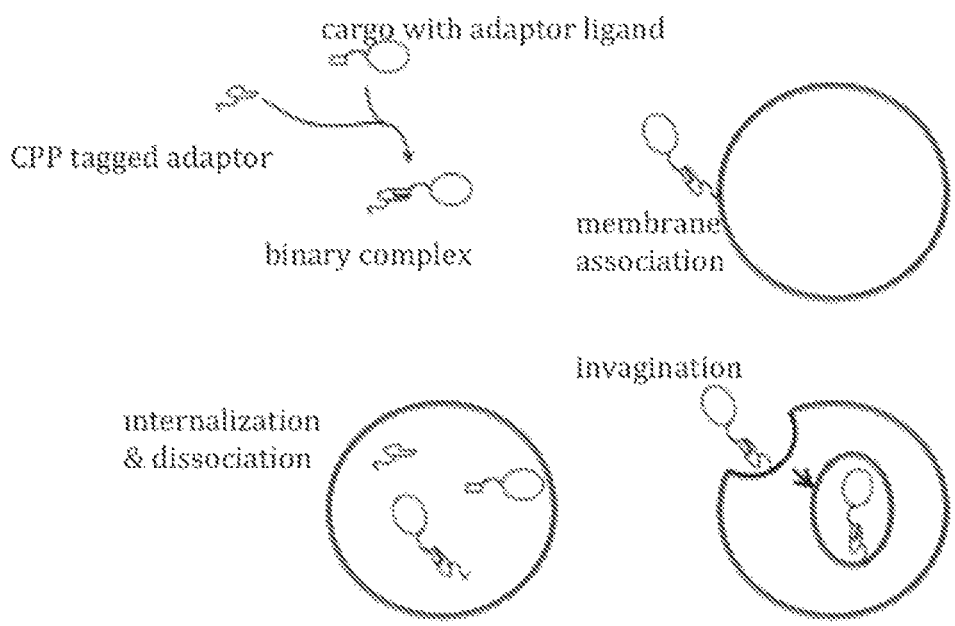
FIG. 2 shows one scheme for the adapter mediated cellular uptake of cargo; association can be mediated by protein-protein or protein-ligand interactions. Clockwise from upper left, association mediated by protein-protein or protein-ligand interactions, binding to cell membrane, internalization, and redistribution to internal compartments.

FIG. 1 shows a scheme for the uptake of cargo, e.g., payload, covalently tagged with a cell penetrating peptide (CPP) by cells. The inventive system and method uses adapters that provide strong protein-protein interactions as a convenient and powerful method to perturb cell interiors with a broad palette of selectively membrane permeable probes (FIG. 2). Common and inexpensively produced adapters are modified by introducing a CPP tag, enabling any protein that binds the adapter to be moved into cells. It is relatively easy and safe to express and purify proteins with a tag that binds to a coupling protein with high affinity. Some tags allow rapid purification of the protein chosen for delivery using a one-step affinity column.

Delivery of proteins to the interior of cells has numerous applications. In addition to mapping the location of the components of living cells with fluorescent tags, the availability of a system capable of translocating proteins into the cell interior enables detection of internal components in real time in living cells, and provides tools for manipulation of signaling pathways and gene expression by allowing the introduction of constitutively active kinases, repressors, and enhancers. Viruses may be intracellularly detected and destroyed. The metabolic state and/or expression profiles of cells may be altered, resulting in wide medical application.

Green Fluorescent Protein (GFP) and other fluorescent proteins may be tagged. GFP and engineered variants and homologs, are powerful tools for cellular interior labeling; they are readily purified. GFP is typically expressed after transfection with the appropriate vector, but many cell types are resistant to transfection. In one embodiment, the cargo delivered is a fluorescent probe such as a GFP fusion containing a site that recognizes an internal target and a tag recognized by a CPP adapter, e.g., a calmodulin binding peptide recognized by TAT-CaM. Such probes are widely used, in part because they can be expressed in mammalian cells after transfection with a shuttle vector, and spontaneously generate a fluorophore inside the cells. The ability to deliver external probes broadens the possibilities.

Figure 3A:
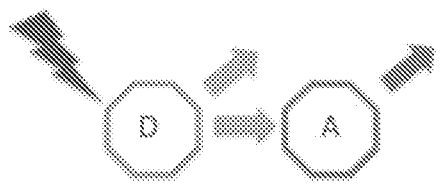
FIGS. 3A and 3B show the basic fluorescence resonance energy transfer (FRET) experiment to detect protein-protein interactions.
Figure 3B:

Many protein types can be labeled with commercially available custom fluorophores, e.g., the Alexa series, and introduced into the cell interior compartments with CPP tags. Tagged proteins may be followed in the cell with confocal microscopy. More demanding investigations including FRET and fluorescence lifetime experiments may be performed. As FIGS. 3A and 3B show, in FRET experiments, components are labeled with fluorophores chosen so that the emission spectrum of one, the donor D, is heavily overlapped with the excitation spectrum of the other, the acceptor A. If the labeled molecules associate in the cell, Forster energy transfer will cause the acceptor to fluoresce when the donor is excited by pumping its absorbance lines, as FIG. 3A shows. If D and A are not in proximity, there is no emission from A, as FIG. 3B shows. This provides information about complex formation in cells. FRET experiments can be performed inside cells using two different GFP variants, but it would be advantageous to use CPP adapters to deliver a pair of proteins labeled with different synthetic fluorophores. Paired fluorophores optimized for FRET, such as Alexa and DyLight® dye, have far better properties, e.g., yield and spectral overlap, than the engineered GFP variants. An important advantage is that they are small and introduce much less steric interference than a GFP fusion.

In lifetime experiments, a fluorophore is repeatedly excited by a pulse from a laser and the fluorescence decays are collected, yielding the lifetimes of the fluorophore in all environments. Typically three or four environments can be readily distinguished with lifetimes in the 50 ps to 5 ns range and contributions as low as a few percent.

Calmodulin is remarkable for its high sequence conservation; only four other proteins are more conserved in eukaryotes. Mammalian calmodulins are identical, and C. elegans calmodulin is 96% identical to its human homolog. Sequence homology conservation is primarily driven by retention of target specificity, not by the requirement for calcium binding and associated organization into the characteristic dumbbell shape. Because calmodulin binds to many Ca2+ activated targets in cells, the ability of the targets and calmodulin to co-evolve is severely restricted.

Figure 4A:
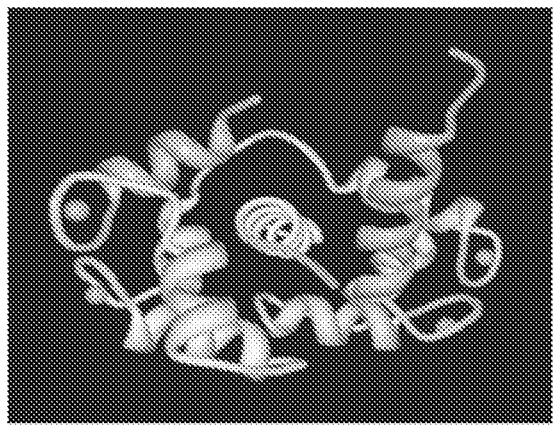
FIGS. 4A and 4B show ribbon representations of the three dimensional structure of calmodulin (CaM), used here as an adapter. Structures of Ca2+-CaM bound to a canonical target peptide in the center of the molecule (FIG. 4A) and in the dumbbell-shaped conformation in the absence of target (FIG. 4B). The central helix breaks during recognition and binding, allowing calmodulin to wrap around the target. Ca2+ are shown as small spheres; the protein is less ordered in the absence of Ca2+(not shown). Free N and C termini are visible.
Figure 4B:
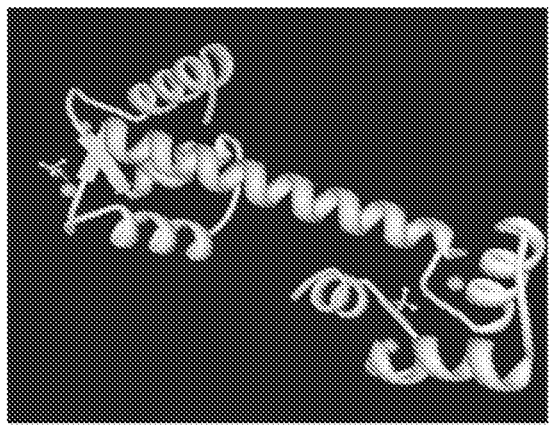

FIGS. 4A and 4B show structures of calcium-calmodulin bound to a canonical target peptide (FIG. 4A) and in the dumbbell-shaped conformation in the absence of target (FIG. 4B). The central helix breaks during recognition and binding, allowing calmodulin to wrap around the target. The protein is less ordered in the absence of calcium (not shown).

As the FIG. 5 alignment shows, sequence similarity within the calmodulin-EF hand superfamily is much lower; identity within the four human sequences shown is about 20%. The sequence variation within the superfamily allows members to recognize and regulate distinct targets in response to a single ionic signal. It permits using the different specificity of superfamily members to produce EF hand based adapters that are specific to different target sequences; all these targets are about 17 AA in length because of the dimensions of the folded EF hand proteins, but the amino acid sequences of the targets are different. This is important because it confers potential to address different cargos to different cellular compartments. FIG. 6 shows the amino acid sequence of TAT-CaM, a CPP tagged calmodulin. The short CPP binding sequence (SEQ ID NO: 26) is located directly before the NOT1 site, which is followed by CaM (SEQ ID NO: 21).

Target proteins are delivered to the interior of cells with CPP labeled calmodulin. Initial demonstrations were designed to use neuronal nitric oxide synthase (nNOS) and CaM kinase; both enzymes are activated by calcium/calmodulin, and both can be purified on a calmodulin column. CaM kinase isoforms have monomer molecular masses of about 41 kDa; the truncated CaM kinase II (New England Biolabs) has a molecular mass of 36 kDa. However, CaM kinases form very large quartenary complexes of 400 kDa-600 kDa, making them an exacting test for the calmodulin mediated translocation system, comparable to beta-galactosidase. The nNOS active dimer has a molecular mass of about 322 kDa. Both nNOS and CaM kinase proteins can be readily labeled with high quantum yield fluorophores that have distinctive spectral signatures, allowing evaluation of their uptake and cellular distribution. These target proteins were selected because they contain a calmodulin binding motif, but most proteins can be produced with a small calmodulin binding tag at the N or C terminus without significantly affecting their activity, or like nNOS with an internal tag associated with an exposed surface loop.

Figure 7A:
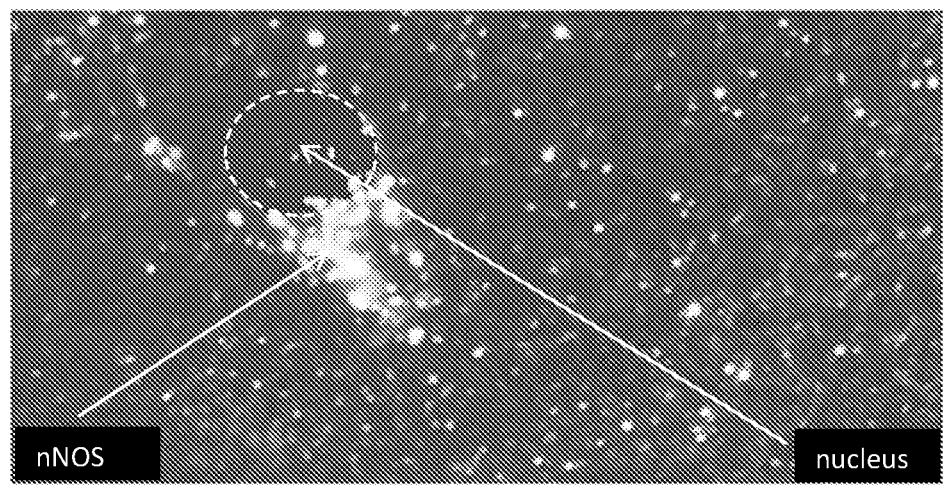
FIGS. 7A and 7B show confocal microscopy images demonstrating uptake of a fluorescence labeled enzyme, neuronal nitric oxide synthase (nNOS), mediated by a CPP linked calmodulin adapter. Projection confocal image of labeled nNOS three hours after onset of TAT-CaM mediated uptake by BHO cells. The indicated nucleus is stained blue; labeled nNOS is stained yellow with DyLight® 540.
Figure 7B:
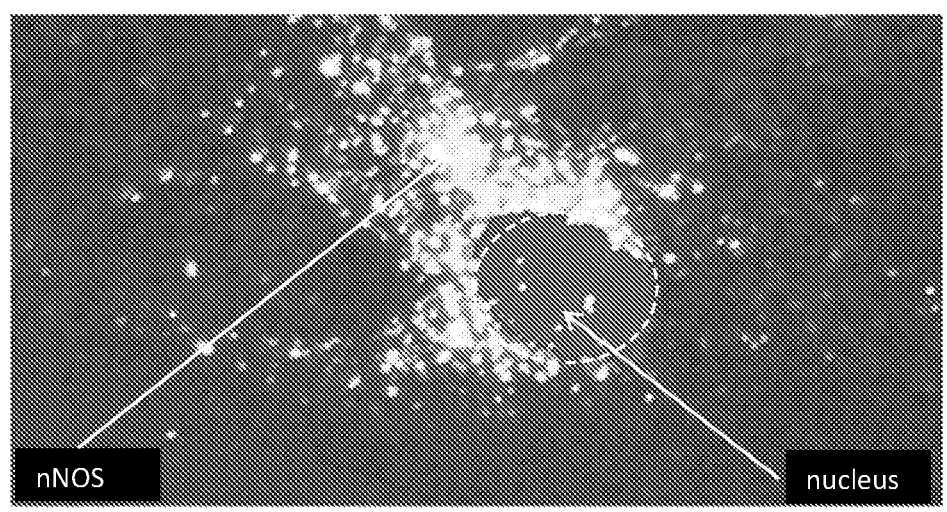

FIGS. 7A and 7B show confocal microscopy images demonstrating uptake of a fluorescence labeled enzyme, neuronal nitric oxide synthase (nNOS), mediated by a CPP linked calmodulin adapter. Projection confocal image of labeled nNOS three hours after onset of TAT-CaM mediated uptake by BHO cells. The indicated nucleus is stained blue; labeled nNOS is stained yellow with DyLight® 540 dye. FIG. 7A shows nNOS added without CPP adapter. Background still shows stained nNOS after washing with media. Some nNOS adheres to the cell surface; three-dimensional cross sections show no nNOS inside cells. FIG. 7B shows that in the presence of TAT-CaM, a large amount of nNOS is rapidly and actively pumped inside the cell, clearing the intracellular space and protecting nNOS from removal by washing. The cell boundary is now visible because cytoplasm is stained by released nNOS. three dimensional cross sections confirm that labeled nNOS is inside the cells. Circles (yellow) inside cells are labeled endosomes.

There was rapid uptake of a novel cargo in which a calmodulin binding site is attached to cargos of myoglobin, horseradish peroxidase, and b-galactosidase. All these cargos are rapidly taken up by mammalian cells, and all rapidly enter the cytoplasm. Calcium triggered release solves the endosomal entrapment problem because cargos are released from trapped CPP when the calcium concentration drops. This is evidenced by cargo escape from endosomes to the cytoplasm while TAT-CaM remains trapped, as shown below in FIG. 9.

TAT tagged calmodulin was initially produced as purified His-tagged calmodulin using His tag and nickel column. Calmodulin binding site-containing cargos may be purified using a calmodulin affinity column, a 17 amino acid canonical sequence calmodulin binding sequence bound with high affinity in the presence of calcium. Calmodulin without the His tag can be produced by affinity chromatography, binding to the column in the presence of calcium, and eluting with the calcium ionophore EDTA.

Figure 8C:
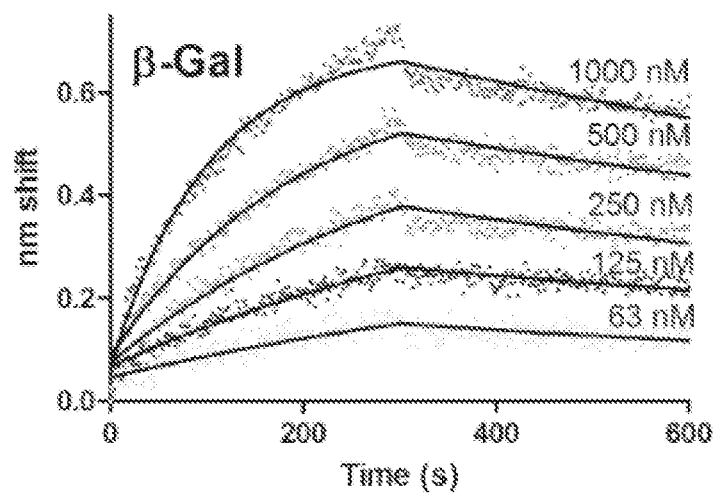
Figure 8D:
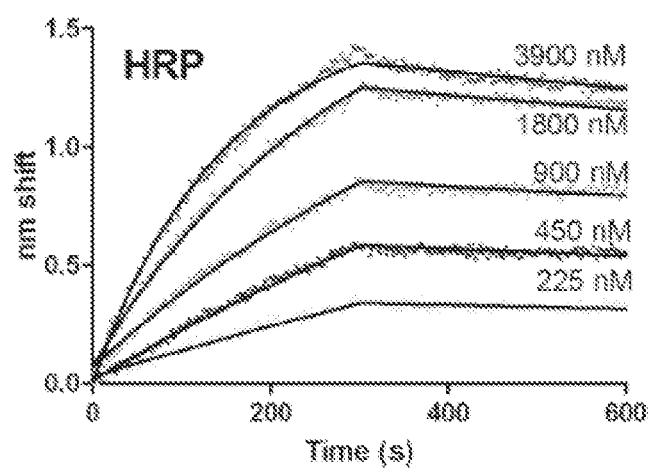
Figure 8E:
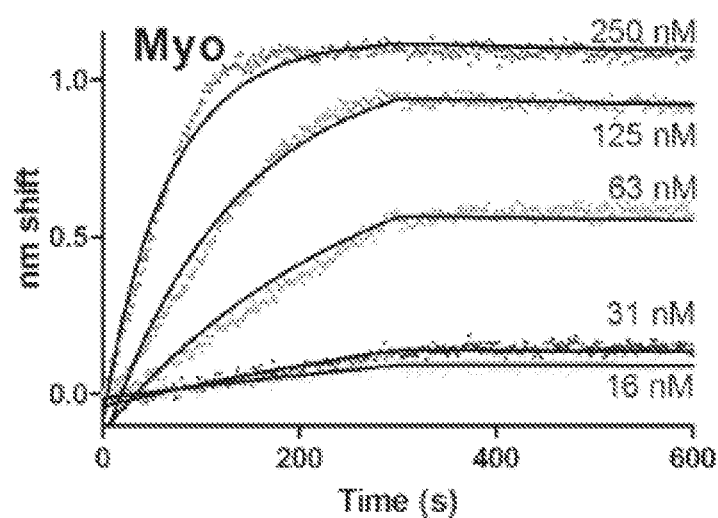
Figure 8F:
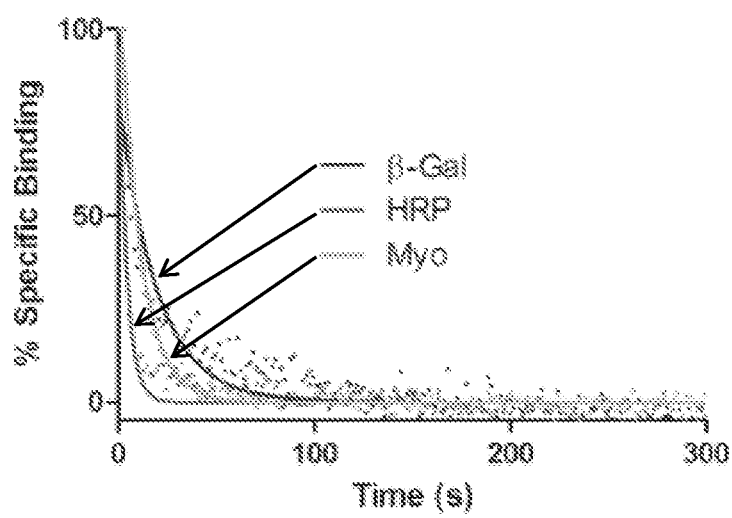

FIG. 8A shows design of TAT-CaM and cargo proteins, according to one embodiment, schematic of TAT-CaM and cargo proteins with amino termini at left. FIGS. 8B-8E show biolayer interferometry (BLI) analysis of TAT-CaM binding to (FIG. 8B) purified endothelial nitric oxide synthase; (FIG. 8C) CBS-β-Gal; (FIG. 8D) CBS-HRP; and (FIG. 8E) CBS-myoglobin. Biolayer interferometry (BLI) was performed using a FortéBio (Menlo Park Calif., USA) Octet QK using SA sensors. Assays were done in 96 well plates at 250 C. Volumes of 200 μL were used in each well. Ligands were loaded onto sensors for 300-900 s followed by baseline measurements in binding buffer (10 mM HEPES pH 7.4, 150 mM NaCl, 10% glycerol) for 300 s. Association was measured by dipping sensors into solutions of analyte protein and was followed by moving sensors to buffer only to monitor dissociation. Binding was fit to a global 1:1 association-then-dissociation model using GraphPad Prism 5.02. TAT-CaM was biotinylated and bound to streptavidin (SA) sensors. Reference-subtracted raw data are rendered as points with fits to a global single-state association-then-dissociation model. Analyte concentrations are noted for each trace. Association and dissociation phases were 300s in length. FIG. 8F shows that after dissociation in buffer only, sensors were moved to buffer containing 10 mM EDTA. The rapid dissociation phases of the 1 μM samples for each cargo protein are shown. Binding is shown as % specific binding to reconcile the varying magnitudes of different analytes.

The prototype CPP-adapter, TAT-CaM (New Echota Biotechnology, Georgia USA), is encoded by a pET19b-based vector containing a cleavable His-tag, the cell penetrating sequence from the HIV transactivator of transcription fused to calmodulin via a GGR linker. Calmodulin was selected as the prototype because mammalian cells typically maintain low resting cytoplasmic Ca2+ levels, allowing rapid release of cargo after internalization. TAT-CaM was expressed and purified from *E. coli* BL21(DE3)pLysS using metal affinity chromatography without detergents. Cargo proteins were expressed in BL21(DE3)pLysS from pCal-N-FLAG-based plasmids (Agilent Technologies, CA, USA) and included myoglobin (Myo), horse radish peroxidase (HRP) and β-galactosidase (β-Gal), each with an amino-terminal vector-encoded calmodulin binding site (CBS). Proteins were purified over a calmodulin sepharose column (GE Healthcare) and exchanged into binding buffer (10 mM HEPES, pH 7.4, 150 mM NaCl, 10% glycerol, 1 mM CaCl2). For cell penetration assays, cargo proteins were labelled with DyLight® 550 dye according to the manufacturer's protocol. Unreacted label was removed via a dye binding column.

TAT-CaM bound to endothelial nitric oxide synthase via the native CaM binding site, with affinity similar to wild-type CaM as assayed with biolayer interferometry (BLI), an optical biosensing technique similar to surface plasmon resonance (FIG. 8B). All cargos bound CaM with low nanomolar affinity (FIG. 8C-E). TAT-CaM and cargo proteins dissociated rapidly upon exposure to EDTA (koff ~0.1 s-1, FIG. 8F), i.e. the TAT-CaM-CBS interaction is functioning indistinguishably from wild type CaM. All analytes exhibited negligible binding to sensors without TAT-CaM. Rate and affinity constants determined from single-state global fits are listed in Table S1.

TABLE S1

|  | $K_D$ (nM) | $k_{on}$ ($M^{-1} s^{-1}$) | $k_{off}$ ($s^{-1}$) | $k_{off}$ (EDTA) ($s^{-1}$) |
|---|---|---|---|---|
| eNOS | 15 | $1.2 \times 10^4$ | $1.8 * 10^{-4}$ | ND |
| β-Gal | 73 | $9.2 \times 10^3$ | $6.7 * 10^{-4}$ | 0.05 |
| HRP | 160 | $1.7*10^3$ | $2.8 * 10^{-4}$ | 0.2 |
| Myo | 0.9 | $5.9 \times 10^4$ | $5.5 * 10^{-5}$ | 0.09 |

Kinetic parameters for sensorgrams shown in FIG. 8.
ND, not determined but previously reported to be ~0.11 $s^{-1}$.

For confocal studies, as shown in FIG. 9, 1 μM each of TAT-CaM and fluorescently-labelled cargo protein in buffer containing 1 mM CaCl2 were added to subconfluent BHK cells and incubated for 1 hour, after which cells were washed three times in phosphate buffered saline with 1 mM CaCl2. This produced very high loading suitable for imaging; enzymatic activity requires much smaller levels of Tat-CaM and cargo. Treated cells were washed three times in phosphate buffer which contained 1 mM CaCl2. Cells were labeled with NucBlue® stain (Life Technologies) to visualize the nuclei. Cargo uptake into cell interiors was assayed using an inverted Zeiss LSM700 confocal microscope equipped with a 40× Neofluar-Plan objective (NA=1.3). Pinholes for each fluorophore were set at 1.0 Airy Units (29 microns), and SP 490 and LP 615 filters were used to acquire the NucBlue® stain (Blue channel) and DyLight® 550 dye (Red Channel) signals, respectively. Z-stacks of both Tat-CaM treated and untreated cells were acquired, and later analyzed for incorporation of fluorescently labeled cargo into the cytoplasm. Orthogonal projections of Z-stacks were then generated using Zeiss ZEN software, which allowed for viewing both treated and untreated cells alike at the same depth within the cell, relative to the diameter of the nucleus. Using the diameter of the nucleus as a landmark, the Z-plane chosen for analysis corresponded to approximately the midpoint depth of the nucleus. Finally, the DyLight® 550 signal was analyzed separately (FIG. 9, left panel, white signal), and merged with NucBlue® (FIG. 9, right panel, red (DyLight® 550) and white (NucBlue®), respectively).

Figure 9A:
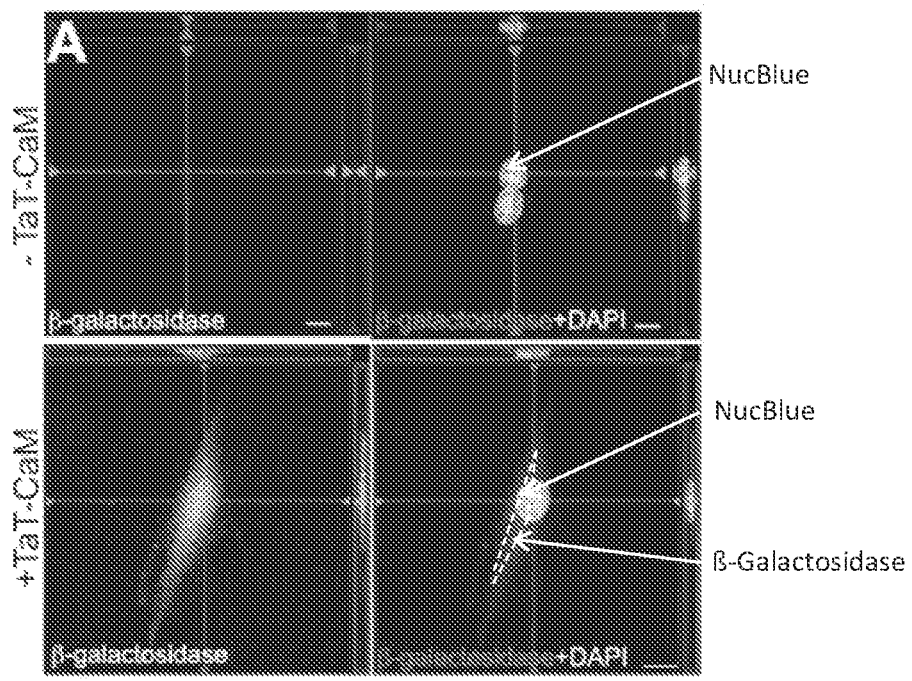
FIGS. 9A-9C show confocal imaging of cell penetration, where the cargo is β-galactosidase (FIG. 9A), HRP (FIG. 9B), and myoglobin (FIG. 9C).
Figure 9B:
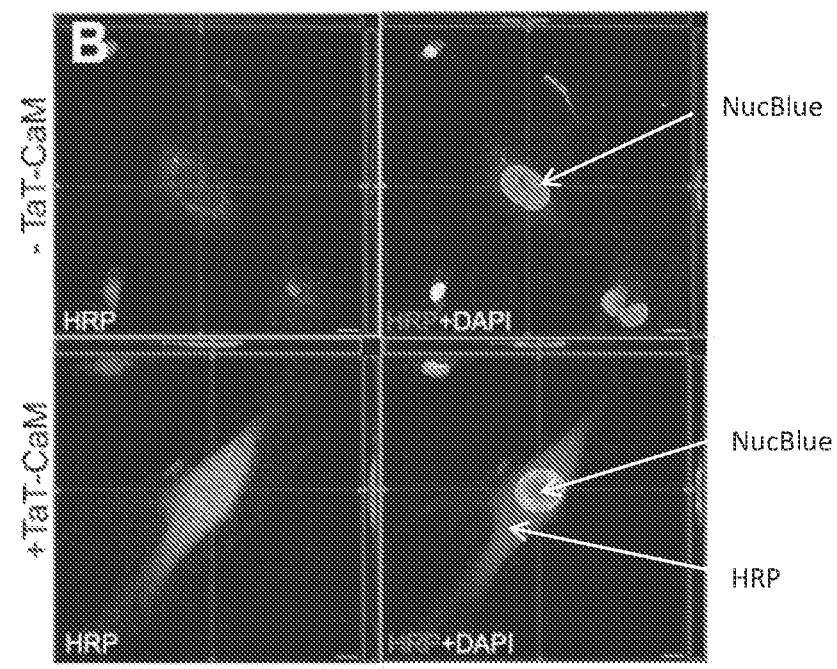
Figure 9C:
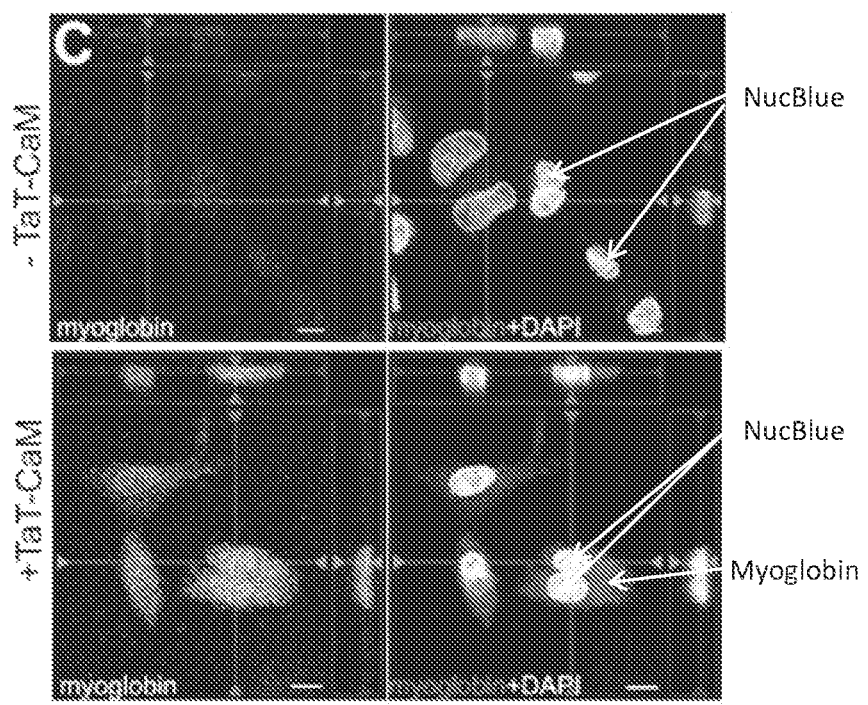

FIGS. 9A-C show confocal imaging of cell penetration, where the cargo is (β-galactosidase (FIG. 9A), HRP (FIG. 9B), and myoglobin (FIG. 9C). BHK cells were treated for 1 hour with the indicated DyLight® 550 fluorescently labeled cargo proteins (white in left panel, red channel in right panel), in either the absence or presence of TAT-CaM, washed and imaged live. Orthogonal projections were generated and the center images presented are optical sections set at a similar depth of the nucleus (NucBlue® staining, white, right panel), as determined by position within the Z-stack. Comparison of TAT-CaM-treated vs. untreated cells indicates that cargo proteins are entering into the cell, and are localized primarily to the cytoplasm. Scale bars in all panels=20 μm.

As shown in FIG. 9, all cargo proteins were delivered to the interiors of the cells and showed significant cytoplasmic distribution, indicating efficient penetration and escape from endosomes. The fluorescently labelled cargo proteins without TAT-CaM showed some adherence to the surfaces of cells, but no discernable penetration at the same cytoplasmic depth as that observed cells treated with TAT-CaM (FIG. 9A-C).

The alternative of CPP directly attached to a cargo, and previous work using CPP attached to cargoes by covalent or, in a few cases, non-specific non-covalent interactions, have several drawbacks. One drawback is additional handing of potentially toxic CPP. Another drawback is CPP remaining on the tag after internalization, causing the cargo to remain associated with the input machinery and preventing endosomal escape. Previous methods require toxic, laborious, and irreversible covalent crosslinking or assembly of irreversible hydrophobic complexes.

In one embodiment, the cargo is tagged with an adapter recognized moiety (e.g., a calmodulin binding peptide) using standard cross linking methods. This embodiment is an alternative to integrated affinity purification and CPP-adapter attachment for proteins that are produced in-house. For example, any commercial proteins, even lacking a CaM binding site, can readily be tagged and rendered cell permeable by covalent crosslinking.

Cell penetrating agents mediate penetration of the plasma membrane, allowing delivery of macromolecular cargos to cell interiors. However, until this invention, cell penetrating agents such as CPP have lagged in development for each of research, diagnostic, and therapeutic applications, hindered by their poor cargo delivery and lack of release. With the inventive system and method, there is efficient intracellular delivery and endosomal escape of user-defined cargos, including but not limited to protein cargos. For example, three different cargo proteins were successfully delivered to the cytoplasm of BHK cells, demonstrating feasibility of numerous applications in living cells including alteration of signaling pathways and gene expression.

While there are over 25 CPP clinical trials underway, including one in Phase III, CPP have largely disappointed for reasons including non-penetration, limited endosomal escape, and requirements for hydrophobic cargos. The disclosed invention is a novel technology that solves or ameliorates all of these problems using a novel CPP-adapter protein fusion. TAT-Calmodulin (TAT-CaM) is used to non-covalently bind, deliver and release cargo into the cytoplasm. The strategy is generally applicable to any soluble protein and also be used to deliver non-protein cargos. Assays can be performed in real time with live cells without significant cytotoxicity. The invention greatly expands the applications of CPPs.

Figure 10A:
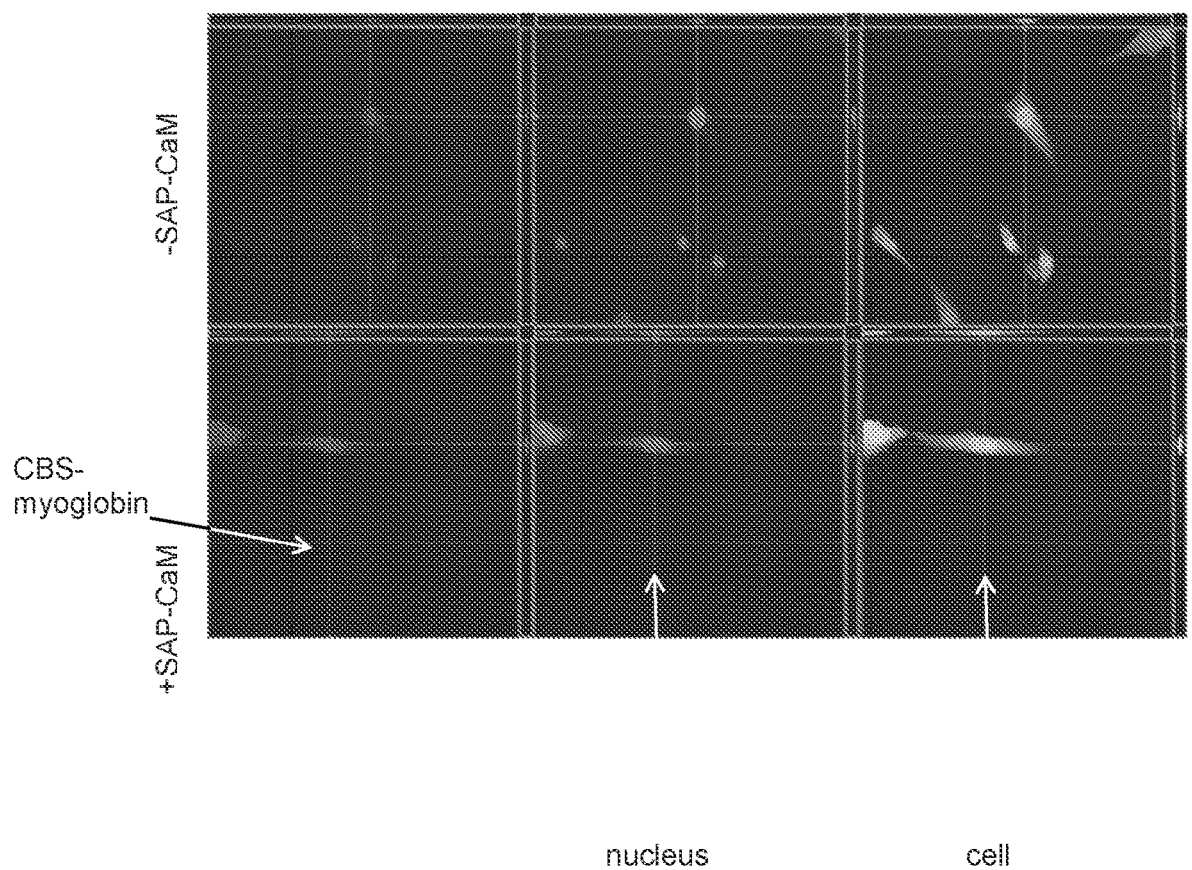
FIGS. 10A and 10B show cell penetration assay for SAP-CaM (FIG. 10A) and SAP(E)-CaM (FIG. 10B) using fluorescently labelled CBS-myoglobin as cargo.
Figure 10B:
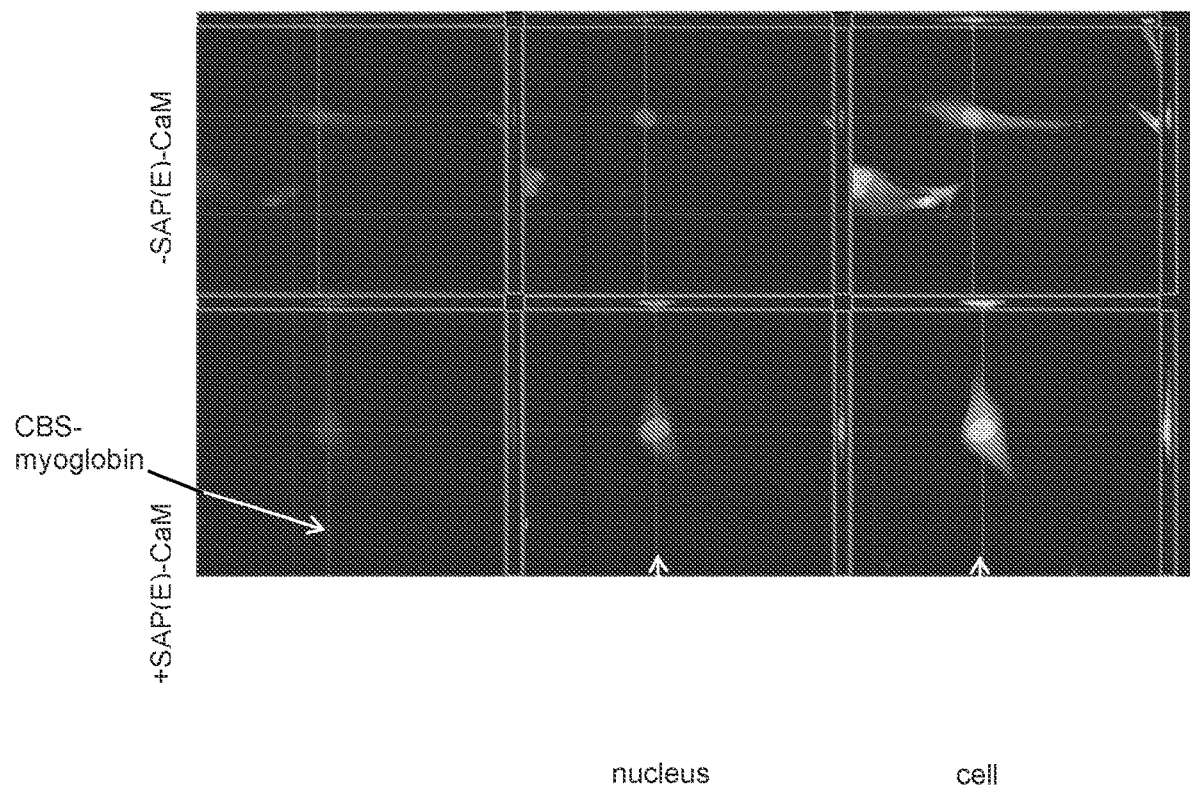

As described above, CPP other than TAT can also be used. FIG. 10 shows results of a cell penetration assay for SAP-CaM (FIG. 10A) and SAP(E)-CaM (FIG. 10B) using fluorescently labelled CBS-myoglobin as cargo. BHK cells were treated for one hour with DyLight® 550 fluorescently labeled cargo protein CBS-myoglobin. The images are optical sections set at a similar depth of the nucleus. DyLight® 550-tagged CBS-myoglobin is shown (left panel), nuclei are stained with NucBlue® (center panel), and the cytoplasm is marked with CellTracker Green CMFDA dye (right panel). Orthogonal projections are shown to the right and top of each panel, demonstrating that the cargo penetrated the cell and was distributed throughout the cytoplasm, as opposed to adhered to the outside of the cell; see '+SAP-CaM' (FIG. 10A) and '+SAP(E)-CaM' (FIG. 10B). Control experiments without CPP-adapter are labelled '-SAP-CaM' (FIG. 10A) and '-SAP(E)-CaM' (FIG. 10B), and show no significant penetration, as expected.

FIG. 11 shows biolayer interferomtery (BLI) analysis of sensorgrams of additional described constructs. FIG. 11A shows TAT-CaM 2.0 (a modified version of TAT-CaM of FIG. 6, where the NotI site, and the GGR it encoded, are removed), FIG. 11B shows TAT-calmodulin like protein 3, FIG. 11C shows SAP-CaM, FIG. 11D shows SAP(E)-CaM, and FIG. 11E shows TAT-troponin. Ligands were biotinylated and tethered to streptavidin sensors. All analytes were CBS-myoglobin except in FIG. 11E using troponin inhibitory peptide-myoglobin. Analyte concentrations ranged from 1 µM to 63 nM, as indicated. Fits are shown to a one-state association-then-dissociation model. Kinetic and affinity constants for CPP-adapter binding to CBS-myoglobin (or TIP-myoglobin) are shown in the table below.

| Constant | TAT-CaM 2.0 | TAT-CALL3 | SAP-CaM | SAP(E)-CaM | TAT-Troponin |
|---|---|---|---|---|---|
| $k_{on}$ (M$^{-1}$s$^{-1}$) | 4900 | 6100 | 8300 | 9400 | 3700 |
| $k_{off}$ (s$^{-1}$) | ND | $1.8 \times 10^{-4}$ | $1.7 \times 10^{-4}$ | $1.3 \times 10^{-4}$ | ND |
| $K_D$ (nM) | ND | 29.8 | 20.6 | 13.3 | ND |
| $k_{off}$(EDTA) (s$^{-1}$) | 0.17 | 0.07 | 0.11 | 0.20 | 0.018 |

Figure 11A:
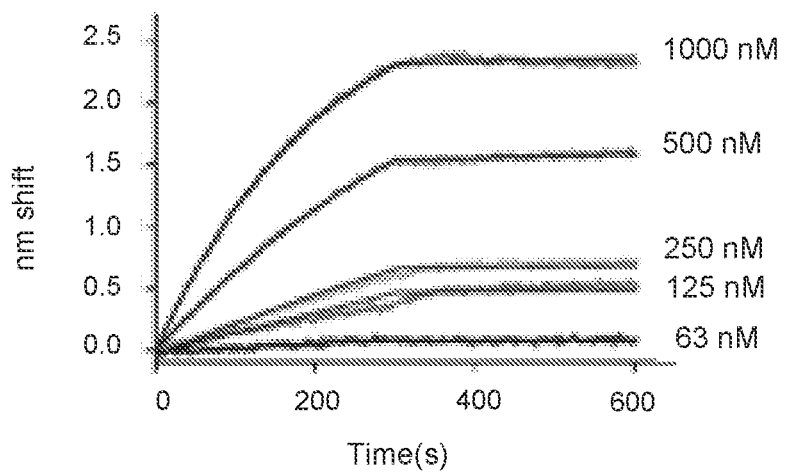
FIGS. 11A-11F show biolayer interferomtery (BLI) analysis of sensorgrams of TAT-CaM 2.0 (FIG. 11A); TAT-calmodulin like protein 3 (FIG. 11B); SAP-CaM (FIG. 11C); SAP(E)-CaM (FIG. 11D); and TAT-troponin (FIG. 11E).
Figure 11B:
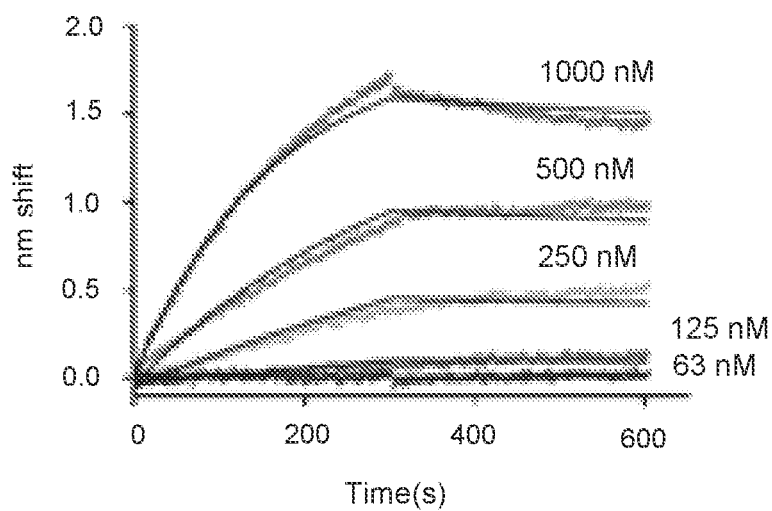
Figure 11C:
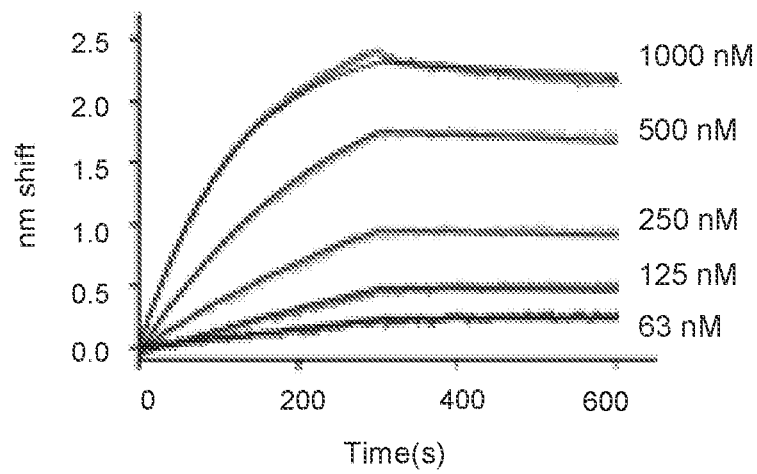
Figure 11D:
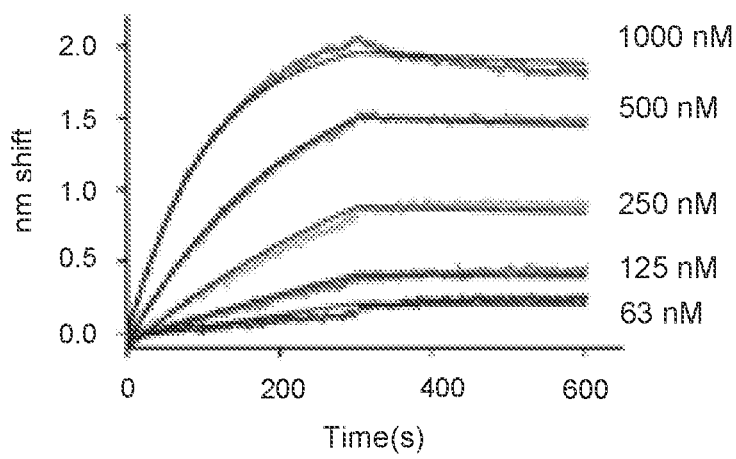
Figure 11E:
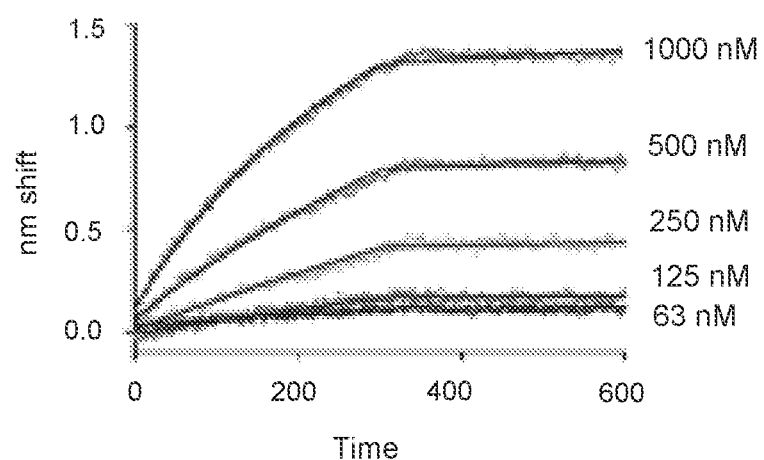
Figure 11F:
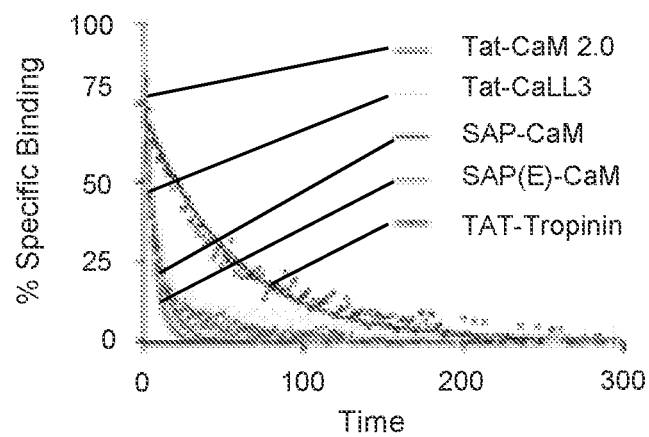

FIG. 11F shows the calcium-dependent binding for all constructs in FIGS. 11A-E, where the sensor was exposed to the highest concentration of analyte in FIGS. 11A-E and was dipped into buffer containing EDTA to remove calcium. Rapid dissociation was observed for each complex (koff about 10-1 s-1 for all except TAT-troponin, which was 1.8×10-2 s-1).

Figure 12A:
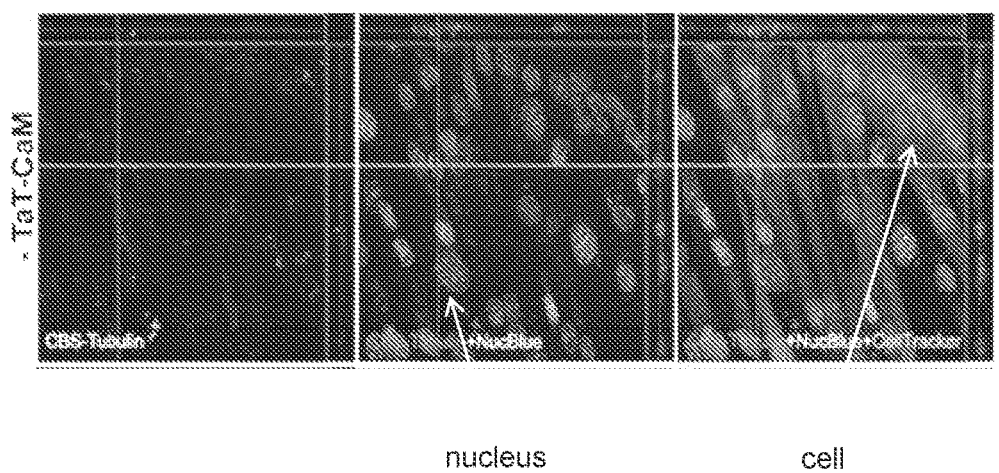
FIGS. 12A and 12B show transport of a cargo, CBS-tubulin, into live myotubes in the presence of TAT-CaM (FIG. 12B) or absence of TAT-CaM (FIG. 12A).
Figure 12B:
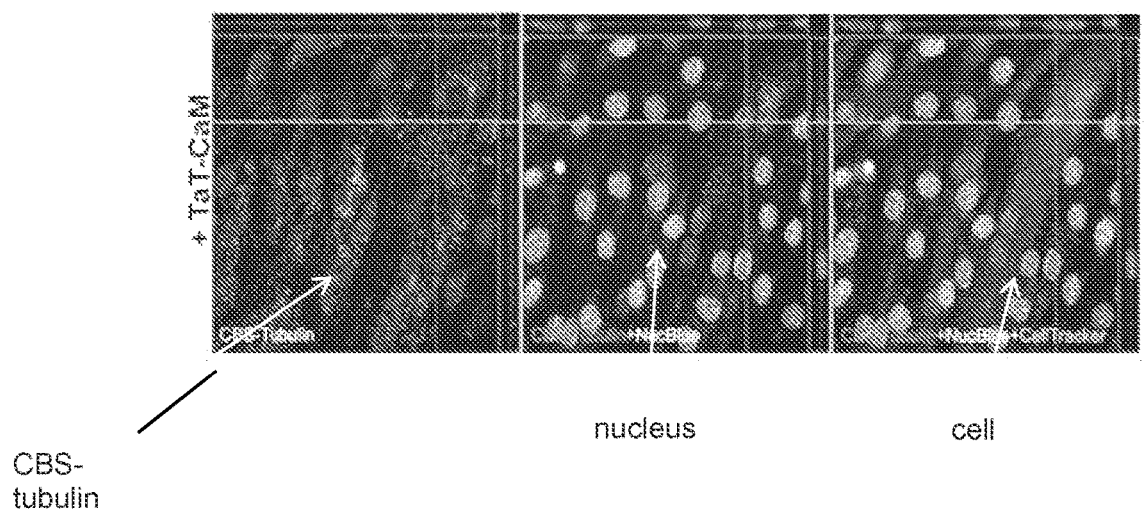

The inventive complexes can be used to introduce a cargo into cells that are difficult to transfect, such as primary cultures. As shown in FIG. 12, the inventive constructs can be used to deliver cargo into myotubes, where myotubes were treated for one hour with DyLight® 550 fluorescently labeled α-tubulin-CBS, in either the absence (FIG. 12A) or presence (FIG. 12B) of TAT-CaM, washed, and imaged live. The center panels show optical sections set at a similar depth of the nucleus (NucBlue® staining shown by arrow in center panel), as determined by position within the Z-stack. Cytoplasmic compartments in live cells were visualized using CellTracker Green CMFDA dye (shown by arrow in right panel). Comparison of TAT-CaM-treated (FIG. 12B) with untreated cells (FIG. 12A) indicates that the cargo protein entered into the cell and localized primarily to the cytoplasm.

In one embodiment, the cargo delivered by the CPP tagged adapter is a modulator, either activator or repressor, of transcription. In one embodiment, the cargo is a probe that measures a property of the cell interior, e.g., an oxidation monitor, NO sensors, pH sensor. In another embodiment, the cargo is a kinase, phosphatase or other enzyme, which may be modified to be constitutively active. In another embodiment, the cargo itself delivers another cargo such as tamavidin, caspase, etc.

Other cargos, including liposomes and their contents, nucleic acids, inhibitors, and drugs can also be delivered by extensions of the same methods, e.g. using DNA binding proteins with calmodulin binding N or C terminal extensions. In one embodiment, the cargo is a nucleic acid delivered using a DNA or RNA binding protein with an adapter binding molecule. In another embodiment, the cargo is a drug or other small molecule delivered using a protein or other scaffold that binds the small molecule and is equipped with an adapter binding molecule.

Secreted peptide hormones such as insulin, bradykinin, EGF, etc. form a large category of endocrine signal molecules controlling diverse and numerous cellular processes. Many of these signal pathways are autoregulated by a negative feedback process that preferentially internalizes hormone receptors with bound ligands.

The inventors were first to recognize and use cell signaling molecules as CPP as cell penetrants. Peptide endocrine and paracrine signals are cell penetrating agents (CPA) if they promote receptor internalization. The prototype is insulin.

Compositions including a CPA-adapter construct combination, such as insulin-calmodulin, are also disclosed. This is a distinct embodiment of the invention, in contrast to CPP-adapter technology using established CPPs, e.g., TAT-calmodulin or TAT-CaM. The embodiments described as using CPPs can also be constructed using CPAs.

In some embodiments, signal molecule-based CPA may not be as effective as existing CPP for general internalization of molecules, but they provide the advantage of specifically targeting the vesicles in which internalized receptors are stored prior to recycling or degradation. This permits specific labeling experiments, FRET experiments, and manipulation of the specific internal compartment to modify the fate of internalized receptors.

Peptide hormones are not unique as endocrine and paracrine signals, and receptors for both larger molecules, e.g., mediating low density lipoprotein uptake or ephrin signaling, and small molecules may be used. Epinephrine in an example of a small molecule endocrine signal that induces receptor internalization. The β-2-adrenergic receptor also serves as a well-established example of G protein coupled receptor internalization in response to a small molecular ligand. Other examples of ligand induced internalization include the folate receptor, the N-methyl-D-aspartic acid (NMDA) receptor, opiate receptors such as MOPr, and the CB1 cannabinoid receptor. All of these ligands are coupled to other proteins, such as the adapter CaM, and used to drive the uptake of cargos into the specific endosomes that contain the ubiquinated receptors. This permits study of trafficking, and also potentially affect the fate of receptors, which can either be recycled or shipped to lysosomes for degradation.

In addition to receptors, transporters are often regulated by ligand activated internalization. Examples include autoregulation of dopamine uptake. This process is initiated by external ligands including cocaine, amphetamines, and melittin. Antidepressants induce internalization of the serotonin transporter in serotonergic neurons. The norepinephrine transporter is also regulated by ligand induced internalization. Specialized cell penetrants may be comparable to the previously disclosed adapters. Other transporters, e.g., the endothelial glucose transporters, are internalized and recycled from the cell interior in response to internal signals, e.g., endothelial glucose transport is regulated by internal glucose. This may be used for, e.g., neuroscience investigations.

The CRISPR/Cas gene editing system is an important advance in research and potential therapeutics. A major obstacle for both is that delivery of CRISPR reagents, e.g. Cas9 and guide RNA, is usually transfection-based, which is difficult or impossible in many situations. The inventive method delivers the components of the CRISPR system, rescuing the function and allowing genome editing in recalcitrant systems.

The clustered regularly interspaced short palindromic repeats, abbreviated CRISPR, are short DNA sequences characterized by repeated palindromic sequences. Palindromic repeats are separated by short DNA spacers, which may have been acquired from viral or plasmid DNA. The CRISPR/Cas system allows prokaryotes to degrade exogenous DNA from plasmids and phages. CRISPR/Cas has been developed as an inexpensive, powerful and transformative gene editing technique due to its wide applicability as a both a tool and potential therapeutic. For gene editing, guide RNA and Cas9 protein must be expressed or delivered to the cell interior.

Figure 13A:
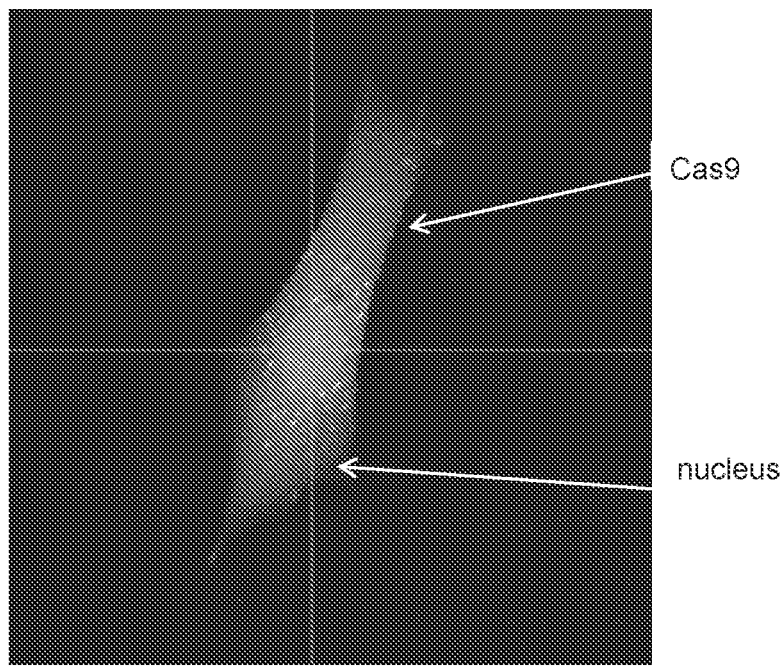
FIGS. 13A and 13B show cell penetration assay for Cas9-CBS in the presence of TAT-CaM (FIG. 13B) or absence of TAT-CaM (FIG. 13A).
Figure 13B:
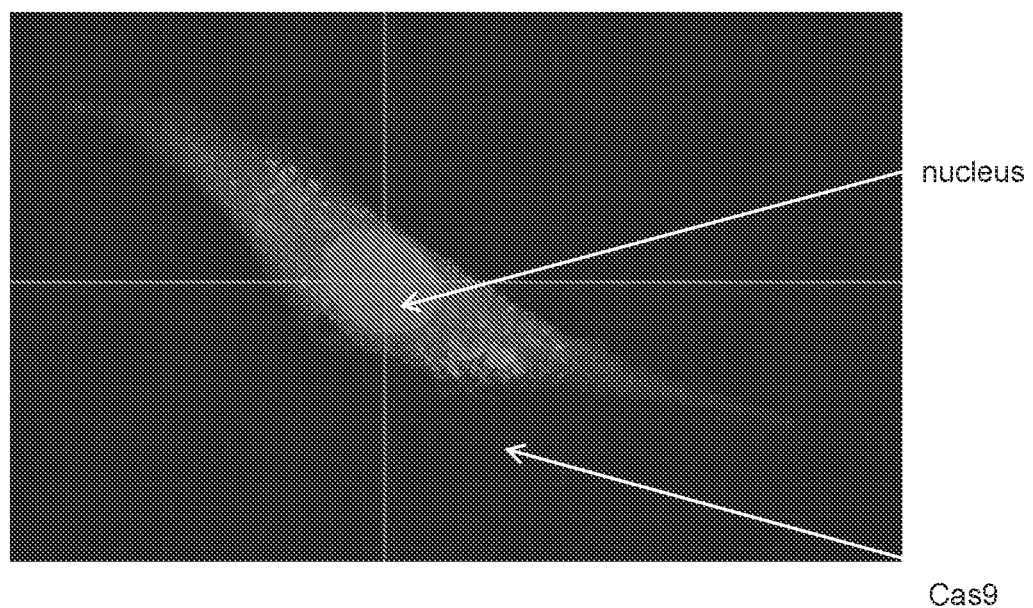

Current use of the CRISPR/Cas system is severely limited by the feasibility of delivering essential components to the cell interior. Delivery is currently by transfection or viral transduction of eukaryotic cells with genes coding for Cas9 and for guide RNA; while effective for some applications, it is unsuccessful in others, either because of inefficient transfection/transduction or poor gene expression. In contrast, as shown in FIG. 13, Cas9 delivery is achieved using the described constructs. Specifically, FIG. 13B shows that, using Cas9-CBS and TAT-CaM, Cas9 was effectively delivered inside BHK cells, where BHK cells were treated for one hour with 1 µM DyLight® 550-labelled Cas9. FIG. 13A shows the control without TAT-CaM.

Figure 14:
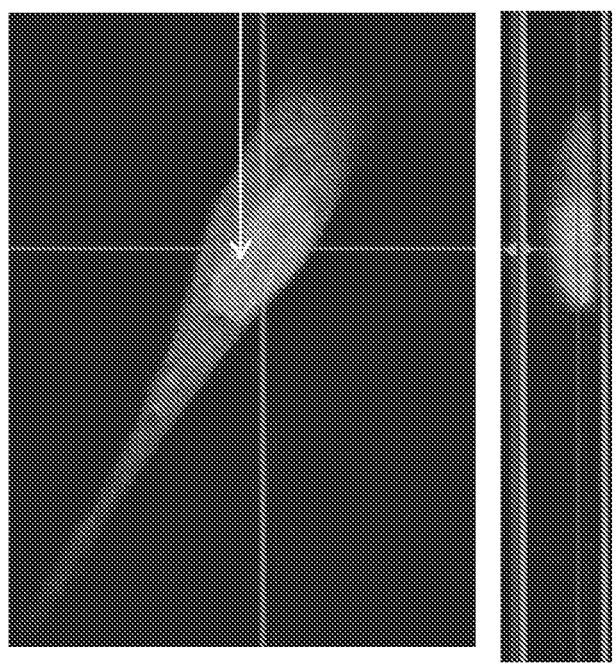
FIG. 14 shows subcellular localization of a cargo comprising a nuclear localization sequence, according to one embodiment.

CPP- or CPA-adapters deliver components to the cytoplasm and target them to specific cellular compartments, including the nucleus. For example, as FIG. 14 shows, a cargo comprising CBS-myoglobin with a consensus nuclear localization sequence from SV40 Large T-antigen (SEQ ID NO: 1), complexed with TAT-CaM, was efficiently transport to the nucleus. Specifically, 1 µM DyLight® 550-labelled CBS-myoglobin with a consensus nuclear localization signal was complexed with 1 µM TAT-CaM and delivered to BHK cells. The cytoplasm is stained with CytoTracker Green, the nucleus with NucBlue and the NLS-CBS-myoglobin in red. The pink color, indicated by the arrow, demonstrated co-localization of DyLight®-labelled CBS-NLS-myoglobin and the NucBlue® nuclear stain, and nuclear localization. The right panel of FIG. 14 shows the orthogonal projection, demonstrating nuclear localization.

This nuclear localization allows the extension of CRISPR/Cas technology to recalcitrant systems. The application of CPP-adapters and CPA-adapters required production of novel Cas protein constructs. In general, such constructs include a Cas protein, an adapter binding site, and a nuclear targeting signal sequence. In one embodiment, the construct contains an N terminal nuclear localization sequence (NLS), a calmodulin binding sequence, and a Cas encoding sequence separated by short spacers. In some cases it may be necessary to also deliver the double stranded RNA component, either with a directly bound adapter recognition tag or using an RNA binding protein.

Figure 15:
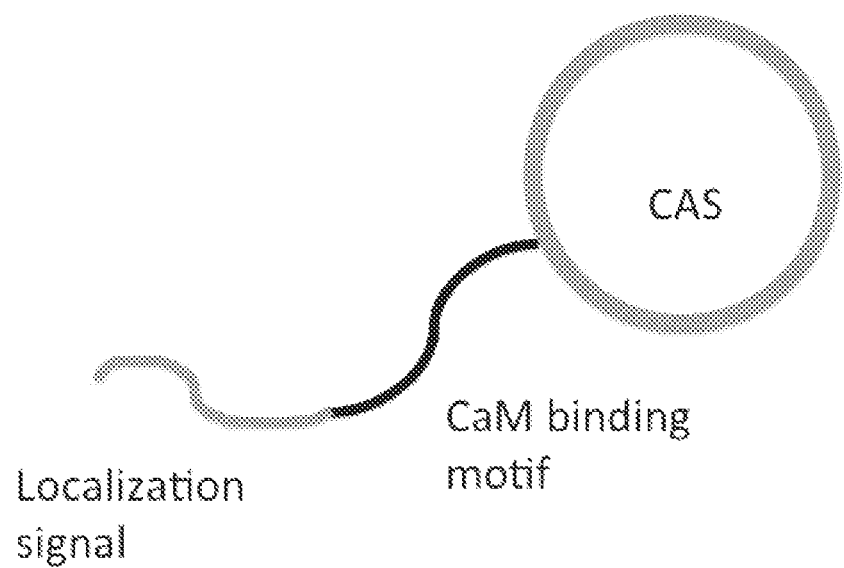
FIG. 15 shows one embodiment of a scheme of a Cas construct for nuclear delivery.

Examples of common nuclear localization sequences include PKKKRKV SEQ ID NO: 1 and KR[PAATKK-AGQA]KKKK SEQ ID NO: 2, a bipartite NLS where the KR and KKKK are the determinant residues. A representative example of a canonical calmodulin binding sequence is the nNOS KRRAIGFKKAEAVFSAKLM SEQ ID NO: 3 sequence (Bredt and Snyder, Proc. Natl. Acad. Sci. 87(2) 682-685 1990). Similar sequences 17-20 residues long are high affinity ligands for calcium replete calmodulin; other CaM binding motifs, e.g., the IQ motif, are also possible. FIG. 15 shows one embodiment of a schematic of a Cas construct for nuclear delivery. This construct can be delivered by the disclosed TAT-CaM CPP adapter system using a construct of the HIV derived CPP TAT and calmodulin.

Outgrowths of CRISPR-Cas include CRISPRi and CRISPR based expression control. In CRISPRi, an inactive Cas is targeted to specific genomic DNA sequences by guide RNA. This technology can be extended by delivering the components to the nucleus using the inventive CPP-adapter technology. This will interfere with expression of a specific gene or genes by preventing transcription through steric inhibition, e.g., of promoter binding. CRISPRi is thus analogous to RNAi suppression of expression, but at the level of transcription rather than translation, useful to target integrated retroviral sequences into the host genome for transcriptionally silencing viral DNA sequences.

In one embodiment, the invention is a composition comprising an inactive Cas analog of the construct shown in FIG. 15, and a method for expression suppression.

Expression controls using Cas-enhancer and Cas-repressor constructs are closely related to CRISPRi. These are targeted by guide RNA to locations adjacent to the binding sites for promoters or enhancers, greatly increasing the effective affinity of these agents for their binding sites on chromosomal DNA. Unlike CRISPRi, downregulation is independent of steric effects by Cas binding and in some cases would be more effective.

It may be desirable to improve delivery of CRISPR guide RNAs to the nucleus. Three potential methods for achieving this are to deliver a preformed Cas-RNA complex, deliver an alternative RNA binding protein complexed with guide RNA, or deliver the guide RNA using a peptide-nucleic acid (PNA) adapter binding moiety bonded to the guide RNA, itself, or to the complement of the guide RNA, which can anneal with a sequence in the RNA. Release of guide RNA from the double-stranded cargo inside the cell can be done by matching the annealing temperature to the experimental conditions. A more effective scheme would lower the temperature of the cells to favor annealing, then return cells to 37° C. to dissociate the cargo RNA from the adapter.

As previously described, cellular internalization is stimulated with ligands and is used to translocate cargo into the cell interior. Not all receptors and transporters are internalized, except on a long time scale as part of general protein turnover. For example, many somatostatin receptor types are not internalized because of ligand binding but their internalization can be forced with CPP attached to receptor ligands by a crosslinker. In one embodiment, a CPP is linked by a crosslinker to a CPA. The structure of the crosslinker may be an amino acid chain 5-20 residues in length, depending on the size of the membrane proteins. Alternatively, materials other than peptide, e.g., carbohydrates, could be employed as a crosslinker. One end of the crosslinker would be covalently attached to a CPP, and one end would be attached to a transporter or receptor ligand or a CPA. An adapter, such as CaM, can be integrated into the linker to allow detachment inside the cell. This is schematically shown as follows:

CPP-crosslinker-transporter
CPP-crosslinker-receptor ligand
CPP-crosslinker-cell penetrating agent Many of the most important techniques available in research and therapeutics are hindered by inability to get nucleic acids across cell membranes. The roster includes transfection of cells with DNA, inhibition of translation, hence expression, by RNAi, CRISPR-Cas editing, and Cas mediated control of expression. Nucleic acid target variants using the inventive system and method solve many of these problems.

Many DNA and RNA binding proteins are available that recognize single or double stranded nucleic acids. A calmodulin binding site (CBS)-nucleic binding protein is a potential vehicle for DNA or RNA import. The drawback is release; reliance on equilibrium either reduces the import efficiency, i.e., low affinity, or slows the release rate, i.e., high affinity. Additional affinity considerations are subsequently disclosed. Some prokaryotic nucleic acid binding proteins are calcium sensitive. The visinin-like protein, important in neurons, is an EF hand protein that binds double stranded RNA, and is a neuron-specific calcium-dependent double-stranded RNA-binding protein. High affinity CaM binding transcription activators provide an alternative strategy; CaMTAs are DNA binding proteins that are calcium activated via Ca+2 release, so low internal calcium would release a CaMTA-nucleic acid complex from TAT-CaM, triggering immediate nucleic acid release from CaMTA.

Figure 16A:
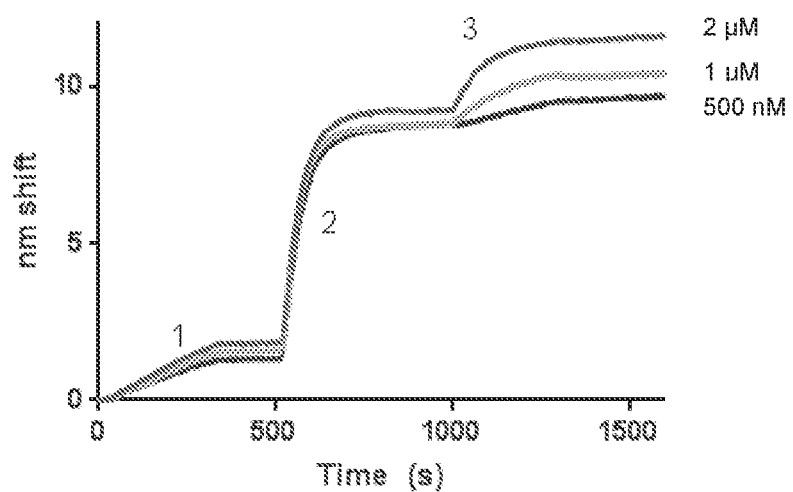
FIGS. 16A and 16B show BLI sensorgram of TAT-CaM/CBS-tamavidin/biotinylated cargo complex assembly (FIG. 16A) and delivery of CBS-tamavidin into BHK cells (FIG. 16B).
Figure 16B:
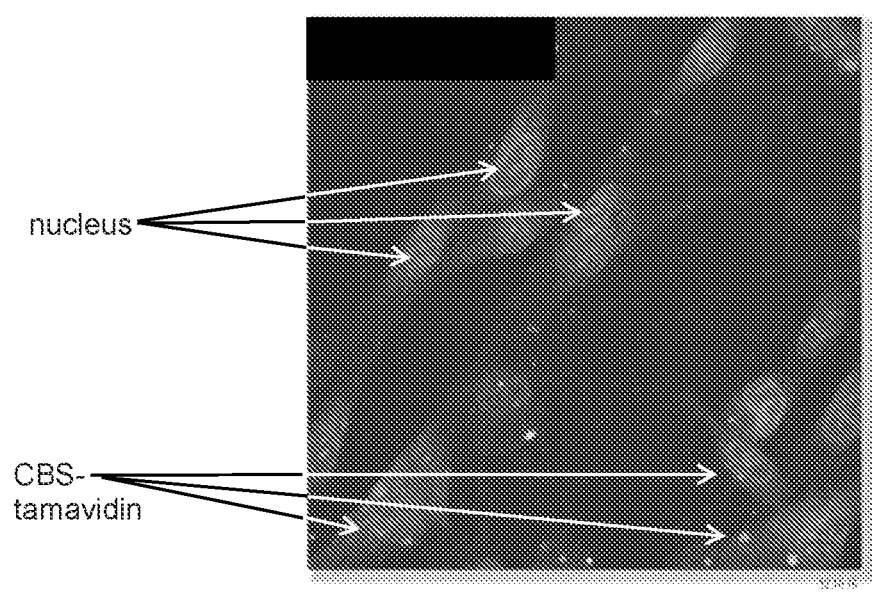

Biotin, a water-soluble B vitamin, is used as a labelling molecule, particularly for end-labeling of synthetic nucleic acids. Avidin, a protein with high affinity for biotin, e.g. streptavidin, is used as biotin-binding proteins in laboratory processes. CPP-adapters can be used in tandem with calmodulin-binding site (CBS)-avidin fusions to bind and deliver biotinylated nucleic acids. CBS-tamavidin has been produced and delivered to BHK cells, as shown in FIG. 16. Specifically, FIG. 16A shows biolayer interferometry sensorgram of TAT-CaM/CBS-tamavidin/biotinylated cargo complex assembly, where phase 1 is TAT-CaM binding to sensors; phase 2 is CBS-tamavidin binding to TAT-CaM; and phase 3 is biotinylated cargo protein binding to CBS-tamavidin. The traces vary only in the concentration of biotinylated cargo protein: 2 µM, 1 µM, and 500 nM, and all data are reference subtracted. CBS-tamavidin did not bind sensors in the absence of TAT-CaM and biotinylated cargo did not bind TAT-CaM-saturated sensors. As FIG. 16B shows, TAT-CaM delivered CBS-tamavidin into BHK cells (CBS-tamavidin and nuclei shown by arrows). Other embodiments include monomeric streptavidins. CBS-avidins can also be used to bind and deliver proteins that are not expressible or active as CBS-fusions but can be biotinylated, e.g. antibodies.

A construct CPP-nucleic acid or CPA-nucleic acid can be made using chemical crosslinking. Such a construct is a CPP or CPA adapter system analogous to TAT-CaM if the nucleic acid is complementary to a sequence in the cargo polynucleotide, allowing duplex formation. An example is a CPP-DNA construct such as TAT-TTTTTTTTTTTT (TAT-SEQ ID NO: 4). Such a construct would bind tightly to the polyA tail of messenger RNA at temperatures below the melting point of the duplex. This can be a mechanism for facilitated endosomal escape, loading at slightly reduced temperatures (25° C.–32° C.) followed by return to 37° C., where the duplex will dissociate. For polyA-polyT interactions, 10-15 bases are likely to be optimal.

```
TAT-TTTTTTTTTTT (TAT-SEQ ID NO: 4)
IIIIIIIIIIII
AAAAAAAAAAAAA-cargo (SEQ ID NO: 5-cargo)
```

Other nucleic acids can be internalized using custom TAT-DNA constructs that anneal to target sequences in the cargo DNA. Alternatively, for applications that tolerate a short additional sequence, e.g., a polyA tail or a shorter CG rich tail, a generic TAT-DNA construct could be used. While TAT-DNA is easier to work with and much less sensitive to degradation, TAT-RNA and TAT morpholinos are also useful.

For cell culture experiments, high affinity between CPP and their target and/or receptor is optimal as long as internal release is sufficiently fast to internalize cargo into internal compartments. This is likely also true for experiments targeting small volumes in large animals, or in experiments with small animals, e.g., C. elegans. For experiments targeting larger volumes, lower affinity CPP are superior because they are not be taken up by the first few layers of cells they encounter. In general, targeting larger volumes of tissue require large amounts of CPP-adapter-cargo complex and CPP with lower affinity. CPP with progressively altered amino acid sequences to obtain altered affinity and kinetics can be evaluated. TAT-CaM delivers cargo to the cytoplasm within about five minutes, and may be in endosomes in about a minute or less. A low affinity mutant of TAT, or another CPP, allows diffusion and circulation to reach a much larger cell population. Constructs similar to TAT CaM may be designed that would act on the time scale of hours.

Conversely, the affinity of the CPP-adapter for the cargo construct should be high to optimize import efficiency; this is very effective for cargos with a built in release, e.g., Ca2+ sensitivity, pH sensitivity, temperature sensitivity, auto-cleavage, etc. For cargo without such a mechanism, a lower affinity would permit a compromise between efficient import into endosomes and release from the membrane. This can be readily accomplished by modifying the linkage between adapter and cargo.

The inventive system and method has use in anti-cancer strategies, including those subsequently described and also those including telomerase suppression, suppression of motility factors that promote metastasis, and suppression or enhancement of oncogene products as appropriate.

The enzyme telomerase extends chromosomal DNA by adding repeats of the sequence TTAGGG as telomeres to the 3' end of chromosomes, non-coding extensions that are progressively removed during cell divisions because of the inability of DNA polymerase to add bases onto the 3' end of DNA. Mammalian telomerases are only active during meiosis, and the length of the telomeric extension determines how many times cells can divide before the coding region is degraded and the cells senesce.

In one embodiment, an active telomerase is delivered to the nucleus, greatly extending the lifetime of cells. Unlike cancer cells, these cells would not be immortalized, because telomerase would not be expressed and the level of activity would fall with time. Cell cultures could be retreated, however, with each treatment extending their life. This is a great advance in cell and tissue culture. In addition, stem cell lifetimes could be greatly extended, not only delaying senescence but producing an essentially unlimited population of cells from a small initial sample. This is of great value for researchers, and allows new therapeutic approaches in diverse areas, e.g., wound healing to anti-agathics.

The inventive system and method enhances existing chemotherapeutic treatment regimens and protocols for the treatment of malignant carcinomas. Many carcinomas result from increased or decreased activity of bHLH transcription factors such as Twist, a developmentally critical transcription factor that, when abnormally regulated, can induce epithelial cells to change from a senescent, sessile state to a malignant motile state. The nuclear transcription co-factors Akirin-1 and/or Akirin-2 is/are a regulator of transcription factor activity in a variety of contexts. Targeting and reducing Akirin-2 levels using nucleic acid-based techniques have been demonstrated to increase sensitivity of Twist-regulated cancer cells in vivo. However, the administration and control of stoichiometry of nucleic acid-based molecules is problematic using conventional technologies.

Using the inventive CPP-based technology overcomes the myriad issues with delivery of nuclei acids to carcinoma cells in vivo. For example, generating a construct consisting of the transcription factor (TF) interacting domain (ID) of Akirin-1 and/or Akirin-2, fused with a nuclear localization signal, cell-penetrating peptide, and CaM binding site (AkirinID-CPP). Using the disclosed inventive delivery system, the fusion protein is introduced to tumor cells including, but not limited to, glioblastoma, neuroblastoma, retinoblastoma tumor cells, and the fusion protein is delivered to the cell and subsequently translocated to the cell nucleus. Once inside the cell, this interaction domain out-competes endogenous TF/Akirin interaction and favors TF/AkirinID-CPP interactions instead, which weakens the tumor cells and renders them more susceptible to parallel treatments. This method is utilized for all potentially mechanistically meaningful domains of Akirin-1 and Akirin-2, once they are identified.

The inventive system and method delivers senescence inducing proteins in virally derived cancers and other antiviral therapeutics, also with research applications.

Cervical carcinoma is the third most common cancer, representing about 16% of all cancers among females. About 90% of cervical cancers are caused by human papilloma virus (HPV), most frequently (75%) by two strains: HPV type 16 and 18. E6 and E7 are the major viral oncogenes. E6 protein binds tumor suppressor p53, targeting it for ubiquitin-mediated degradation. E6 also stimulates telomerase activity. E7 protein binds p105Rb and other retinoblastoma tumor suppressor proteins. The combined effect of the activities of these proteins leads to aggressive proliferation.

Early viral transcription produces E2 protein, which represses expression of E6 and E7. However, during integration into the host chromosome leading to oncogenesis, the gene encoding it is disrupted, which leads to increases in E6 and E7 expression and proliferation. Differential activities of E6 and E7 in HeLa cells were previously characterized and induced replicative senescence by superinfection with a recombinant SV40 virus encoding bovine E2.

Figure 17A:
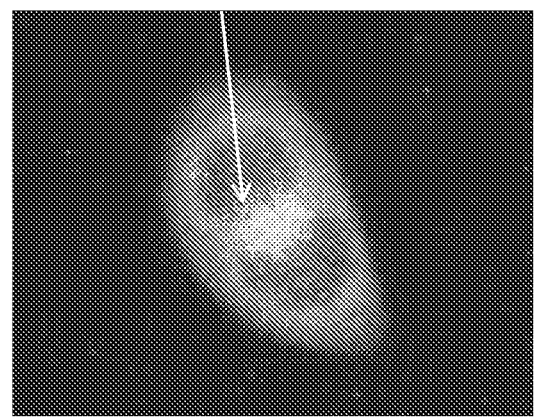
FIGS. 17A-17C show delivery of HPV E2 into SiHa cells (FIG. 17A), induction of senescence in SiHa cells (FIG. 17B), and reduction of metabolic activity (FIG. 17C).
Figure 17B:
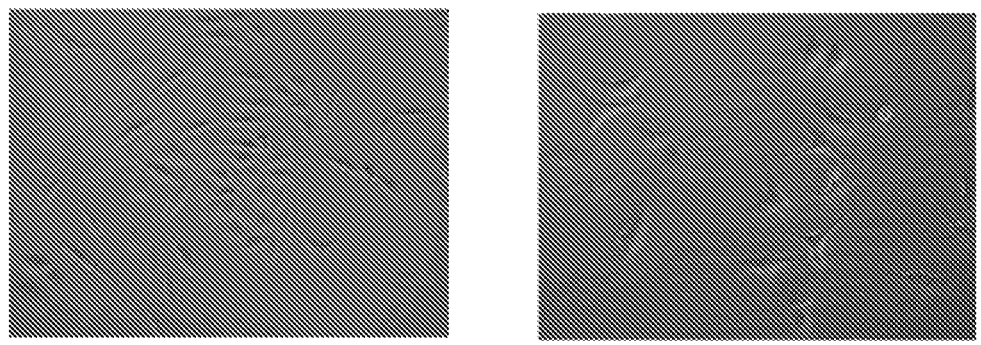
Figure 17C:
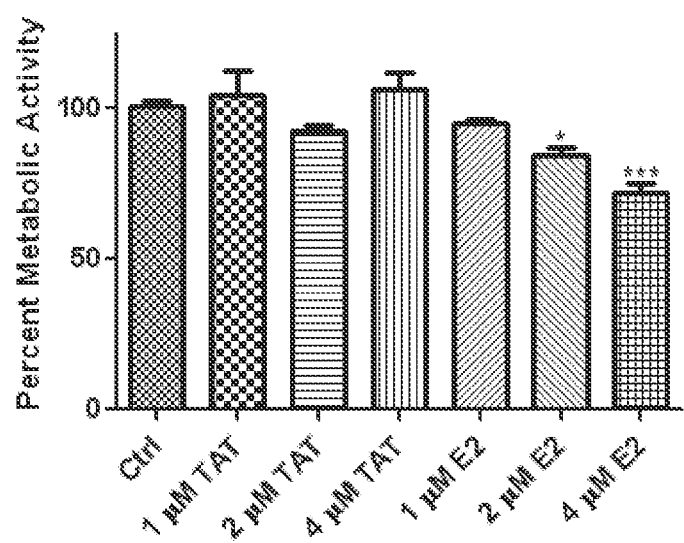
Figure 18:
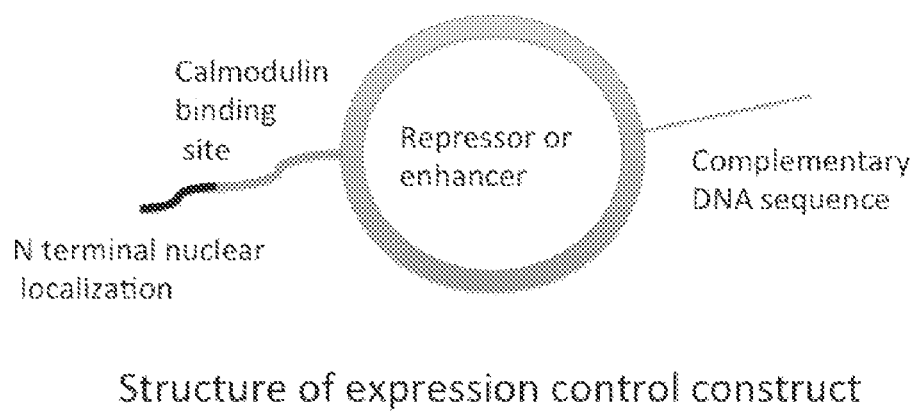
FIG. 18 shows the structure of a targeted expression control construct, according to one embodiment.

The disclosed inventive senescence inducing cargo protein CBS-E2, or calmodulin binding site fused to HPV protein E2, is used in tandem with Tat-CaM. For example, as FIG. 17 shows, TAT-CaM delivered HPV E2 induced senescence in SiHa cells. FIG. 17A shows delivered fluorescently labelled CBS-E2 (indicated by arrow; magenta) aligning on the mitotic plate of a dividing cell. Cytoplasm is marked with CytoTracker Green and nuclei are labeled with NucBlue®. FIG. 17B shows control with TAT-CaM only (left panel), and TAT-CaM/CBS-E2 (right panel), where TAT-CaM/CBS-E2 induced morphological changes indicative of senescence at 72 hr. FIG. 17C shows metabolic activity reduction varies by the concentration of E2, TAT-CaM only controls are insignificantly different from no addition control (Ctrl), and 2 μM and 4 μM E2 caused significantly lower metabolic activity of the affected cells. CPP/E2 offers many advantages over recombinant virus in terms of safety, stability and effective dosing. Applications include, but are not limited to the following:

Elimination of HeLa contamination of cultured cells. HeLa cells, the oldest and most commonly used human cell line, has undergone horizontal gene transfer from HPV18 at five different sites in its hypertriploid genome. It is well adapted to growth in tissue culture plates and easily contaminates other lines, often overgrowing them. Users are often not aware of the overgrowth, leading to devastating but unknown impact on a multitude of projects; one report was 29% of 360 known cross-contaminated cell lines were HeLa contaminated; another report was about 10-20% of all in vitro cell lines are contaminated with HeLa, resulting in numerous artifactual results across a wide array of research efforts. CPP-E2 arrests the proliferation of HeLa in a contaminated cell line while allowing proliferation of the desired cells, eliminating the contamination.

Tissue culture media additive. The stability of CPP-E2 makes it an excellent additive for tissue culture media to prevent HeLa contamination. Its specificity for HPV-infected cells means that it is non-toxic and non-interfering to other types of cells. There is a large and growing global cell culture supplies market.

Topical antiviral. CPP-E2 is soluble, stable and non-toxic. It can be used as an antiviral additive to condom lubricants, diaphragm jellies, contraceptive sponges, representing a significant value-added proposition to the global contraceptives market. CPP-E2 may also be used as an additive to cleaning products.

Anti-cancer therapeutic. Papillomavirus infects keratinocytes, causing skin lesions. Given CPP-EP2 cell-penetrating capabilities, applications are delivery to tumors in vivo for cervical, skin, and other mucosal or cutaneous cancers.

Oncogenesis research tool. Delivery of E6 and E7 can induce immortalization when, paired with induction of senescence, a suite of tools may be produced for study of cellular processes and events surrounding the immortalization/replicative senescence boundary.

Other applications include other antivirals including ones targeted against herpes, HIV, Epstein-Barr, hepatitis B, and hepatitis C.

Targeted expression control. The ability to load constructs directly into cell interiors makes it possible to deploy synthetic cargos not found in nature and which cannot be expressed by transfected cells. Examples of these constructs can be used to up or down regulate expression.

FIG. 18 schematically shows the structure of one embodiment of a targeted expression control construct. The CaM binding site can dock with a construct such as TAT-CaM, importing it into the cell. The N terminal nuclear localization signal targets the construct to the nucleus. In the nucleus, the attached complementary DNA sequence, which can be covalently attached but need not be as long as the attachment is high affinity, binds to a chromosomal sequence 3' to the gene and associated control sequences. This targets the repressor or enhancer to the appropriate binding site, up or down regulating the target gene. In principle, this is similar to CRISPRi but is simplified because only a single molecule is needed rather than inactive mutant Cas and a guide RNA.

Many other applications exist for expression control. Exemplary non-limiting examples include reduction of inflammatory proteins, repression of telomerase in cancer treatment, enhanced production of enzymes where function has been compromised by low expression, etc.

Internalization of antifreeze proteins (AFP) and ice nucleation proteins in organisms living in environments where the ambient temperature is below the freezing point of water; such organisms have evolved antifreeze proteins to prevent cellular damage secondary to ice crystal formation. Antifreeze proteins interact with water molecules to prevent freezing by regulating the formation and shape of ice crystals. AFP may be localized to the extracellular fluid, the cell surface, or intracellularly. Treatment with extracellularly-administered AFPs can improve cryopreservation of embryos and a wide range of cell types. However, treatment with Type 1 AFP has led to increased destruction of some cell types and tissues during freezing, apparently due to formation of needle-like intracellular ice crystals.

Use of the inventive CPP-based technology intracellularly delivers a wide range of AFP into cells destined for cryopreservation, without their genetic modification. An example strategy fuses a calmodulin binding site to an AFP, producing CBS-AFP to be used in tandem with TAT-CAM or other CPP-CAM construct. CBS-AFP has the potential to enhance viability of cryopreserved cells and embryos by regulating intracellular ice formation, and may increase the potential for cryopreservation of whole tissues and organs.

The class of ice nucleation proteins (INP) promote formation of ice crystals. CPP-based delivery of intracellular INP would render cells more susceptible to cold injury. In an analogous example strategy to CBS-AFP, CBS-INP is constructed by fusing a calmodulin binding site to an ice nucleation protein, and delivered intracellularly using TAT-CAM. CBS-INP could be a useful adjuvant to cryosurgery. Oct4, Soc2, Klf4 and c-Myc, the Yamanaka Factors are highly expressed in embryonic stem cells. Their forced expression in differentiated cells can return those cells to a stem cell state, creating induced pluripotent stem cells (iPSC). Previous approaches used retroviral vectors to deliver cDNAs expressing these reprogramming factors. While effective in the laboratory, this gene delivery strategy creates potential problems, particularly if iPSC are to be used in a therapeutic context. The inventive cargo system and method bypasses this issue by delivering proteins directly to the cell. This enormous benefit is extended to the direct reprogramming of differentiated cells into other cell types, e.g., neurons, islet cells, etc.

Other CPP-cargo strategies rely on covalent linkage or nonspecific hydrophobic linkers that are susceptible to getting trapped by membrane association as the CPP itself may not be released into the cytoplasm. Even non-hydrophobic CPP are likely to be tightly bound to membrane proteins associated with the import machinery, which would be expected to greatly hinder endosomal escape by covalently attached cargo proteins. One group estimates that a fraction of 1% of TAT-fused cargos escape endosomes. High-affinity but reversible noncovalent attachment of cargos overcomes trapping effects via Ca2+-dependent dissociation, allowing rapid and efficient cargo distribution to the cytoplasm even though the CPP may remain attached to the membrane.

Cytotoxicity is also a major drawback with current CPP, particularly given the concentrations necessary to attain observable endosomal escape. With cytotoxic effects of TAT becoming significant in the tens of μM, the fact that TAT-CaM effects significant cytoplasmic distribution of cargos at 1 μM without an increase in cell death as measured by Trypan Blue exclusion (data not shown) is particularly exciting. Release of cargo is the rate limiting step in endosomal escape.

The time frame of cargo delivery using CPP-adapters is an hour or less. This contrasts to the time required to transfect cells; CPP-adapter augmentation is roughly two orders of magnitude faster than transfection, making possible time course experiments that could never be previously attempted.

An wide array of applications can be developed from the inventive method and system. CPP-adapters can allow for subcellular addressing, e.g. delivery of a transcription factor to the nucleus, with kinetics, dosing, toxicity and other parameters as well delivery of a wide array of cargos.

SEQUENCE LISTING

The Sequence Listing submitted on Jul. 22, 2020, as a text file named "065848_0011US2_replacement_seqlisting_ST25.txt" created on Jul. 10, 2020, and having a size of 17 KB is hereby incorporated by reference pursuant to 37 C.F.R. § 1.52(e)(5).

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

What is claimed is:

1. A composition for intracellular delivery of a cargo molecule, the composition comprising:
 a cell penetrating peptide (CPP) or cell penetrating agent (CPA) covalently linked to an adapter, and
 a cargo molecule covalently linked to an adapter-binding molecule,
  wherein the composition is formed by a reversible, non-covalent bond between the adapter and adapter-binding molecule,
  wherein the adapter is an EF-hand calcium signaling protein and the adapter-binding molecule is an EF-hand calcium signaling protein binding molecule, and
  wherein the non-covalent bond between the adapter and the adapter-binding molecule is configured to be reversed by intracellular calcium binding to the EF-hand calcium signaling protein.

2. The composition of claim 1, wherein the CPP is selected from the group consisting of Tat, Penetratin, Transportan, Dat, herpes simplex virus protein VP-22 (VP-22), amphipathic peptides, MPG, Pep-1, multiple antigen protein (MAP), sweet arrow peptide (SAP), PPTG1, arginine-rich peptides, oligoarginine, human calcitonin (hCT (9-32)), SynB, and cadherin-5 (Pvec).

3. The composition of claim 1, wherein the CPA is selected from a receptor ligand or transporter ligand.

4. The composition of claim 3, wherein the receptor is selected from the group consisting of insulin receptor, beta 2-adrenergic receptor, folate receptor, the N-methyl-D-aspartic acid (NMDA) receptor, opiate receptors, cannabinoid receptor, and combinations thereof.

5. The composition of claim 3, wherein the transporter is selected from the group consisting of dopamine transporter, serotonin transporter, norepinephrine transporter, endothelial glucose transporter, and combinations thereof.

6. The composition of claim 1, wherein the adapter-binding molecule is further attached to a sequence that localizes the cargo to a cellular location or organelle that is selected from the group consisting of nucleus, peroxisome, mitochondria, endoplasmic reticulum, Golgi, and combinations thereof.

7. The composition of claim 1, wherein the cargo is selected from the group consisting of a protein, a drug, a liposome, a nucleic acid, and combinations thereof.

8. The composition of claim 1, wherein the cargo is a nucleic acid and the adapter-binding molecule is covalently linked to a nucleic acid binding protein.

9. A composition comprising:
 a cell penetrating peptide (CPP) or cell penetrating agent (CPA) covalently linked to an adapter;
 an adapter-binding molecule non-covalently linked to the adapter, wherein the adapter is an EF-hand calcium signaling protein and the adapter-binding molecule is an EF-hand calcium signaling protein binding molecule; and
 a cargo molecule covalently linked to the adapter-binding molecule.

10. The composition of claim 9, wherein the non-covalent bond between the adapter and adapter-binding molecule is configured to be reversed by intracellular calcium binding to the EF-hand calcium signaling protein.

11. The composition of claim 9, wherein the CPP is selected from the group consisting of Tat, Penetratin, Transportan, Dat, herpes simplex virus protein VP-22 (VP-22), amphipathic peptides, MPG, Pep-1, multiple antigen protein (MAP), sweet arrow peptide (SAP), PPTG1, arginine-rich peptides, oligoarginine, human calcitonin (hCT (9-32)), SynB, and cadherin-5 (Pvec).

12. The composition of claim 9, wherein the CPA is selected from a receptor ligand or transporter ligand.

13. The composition of claim 12, wherein the receptor is selected from the group consisting of insulin receptor, beta 2-adrenergic receptor, folate receptor, the N-methyl-D-aspartic acid (NMDA) receptor, opiate receptors, cannabinoid receptor, and combinations thereof.

14. The composition of claim 12, wherein the transporter is selected from the group consisting of dopamine transporter, serotonin transporter, norepinephrine transporter, endothelial glucose transporter, and combinations thereof.

15. The composition of claim 9, wherein the adapter-binding molecule is further attached to a sequence that localizes the cargo to a cellular location or organelle that is selected from the group consisting of nucleus, peroxisome, mitochondria, endoplasmic reticulum, Golgi, and combinations thereof.

16. The composition of claim 9, wherein the cargo is selected from the group consisting of a protein, a drug, a liposome, a nucleic acid, and combinations thereof.

17. The composition of claim 9, wherein the cargo is selected from the group consisting of a modulator of transcription in the cell, a probe that measures a property of the cell interior, and an enzyme.

18. The composition of claim 9, wherein the cargo is a nucleic acid and the adapter-binding molecule is covalently linked to a nucleic acid binding protein.

* * * * *